(12) United States Patent
Grieninger et al.

(10) Patent No.: US 6,416,963 B1
(45) Date of Patent: Jul. 9, 2002

(54) CLEAVED FRAGMENTS OF FIBRINOGEN

(75) Inventors: Gerd Grieninger; Dianne Applegate, both of York, NY (US); Lara Stoike-Steben, Ann Arbor, MI (US)

(73) Assignee: New York Blood Center, New York, NY (US)

( * ) Notice: Subject to any disclaimer, the term of this patent is extended or adjusted under 35 U.S.C. 154(b) by 0 days.

(21) Appl. No.: 09/373,157

(22) Filed: Aug. 12, 1999

Related U.S. Application Data

(60) Provisional application No. 60/096,210, filed on Aug. 12, 1998.

(51) Int. Cl.⁷ ............................................... G01N 33/53
(52) U.S. Cl. ...................... 435/7.92; 435/7.92; 435/7.1; 435/6; 530/350; 530/300; 514/2
(58) Field of Search ............................. 514/2; 435/7.1, 435/6, 7.92; 530/300, 350

(56) References Cited

U.S. PATENT DOCUMENTS 6,025,148 A * 2/2000 Grieninger et al. ......... 435/7.92

FOREIGN PATENT DOCUMENTS

WO      WO 96/41170 A1     12/1996

OTHER PUBLICATIONS

Alignment, Grieninger et al (U.S. Patent 6,025,148), Jul. 1, 1997.*

Applegate, et al., "The $\alpha_E$C domain of human fibrinogen–420 is a stable and early plasmin cleavage product", *Blood*, Apr. 1, 2000 vol. 95, No. 7, 2297–2303.

Spraggon et al., "Crystal structure of a recombinant $\alpha_E$C domain from human fibrinogen–420", *Proc. Natl. Acad. Sci. USA*, Aug. 1998 vol. 95, 9099–9104.

Kant et al., "Partial mRNA sequences for human A$\alpha$, B$\beta$, and $\gamma$ fibrinogen chains: Evolutionary and functional implications", Proc. Natl. Acad. Sci. 80: 3953–3957.

Fu et al., "Carboxy–Terminal–Extended Variant of the Human Fibrinogen $\alpha$ Subunit: A Novel Exon Conferring Marked Homology to $\beta$ and $\gamma$ Subunits" Biochemistry (1992) 31 (48): 11968–72.

* cited by examiner

*Primary Examiner*—Karen Cochrane Carlson
*Assistant Examiner*—Hope A. Robinson
(74) *Attorney, Agent, or Firm*—Hoffmann & Baron, LLP

(57) ABSTRACT

The invention provides novel $\alpha_E$CX cleavage fragments of fibrinogen and methods for detecting and purifying these fragments. The method of the invention also includes a diagnostic method for determining fibrinolytic states or atherogenesis in a mammal. Methods of treating disease characterized by fibrinogen metabolism are also disclosed. In addition, the invention also provides monospecific antibodies which are specifically reactive with $\alpha_E$C domain of fibrinogen. Also provided, are DNA and RNA molecules that encode $\alpha_E$C cleavage fragments of fibrinogen. In addition, the present invention includes a vector and a host cell capable of expressing $\alpha_E$CX cleavage fragments of fibrinogen.

6 Claims, 7 Drawing Sheets

CLEAVED FRAGMENTS OF FIBRINOGEN

This application claims the benefit of U.S. Provisional Application No. 60/096,210, filed Aug. 12, 1998, the entire contents of which is hereby incorporated by reference.

This invention was made in part with Government support under NIH Grant ROIHL51050 awarded by the Public Health Service. The Government has certain rights in this invention.

BACKGROUND OF THE INVENTION

The clotting of blood is part of the body's natural response to injury or trauma. Blood clot formation derives from a series of events called the coagulation cascade, in which the final steps involve the formation of the enzyme thrombin. Thrombin converts circulating fibrinogen into fibrin, a mesh-like structure which forms the insoluble framework of the blood clot. As a part of hemostasis, clot formation is often a life-saving process in response to trauma and serves to arrest the flow of blood from severed vasculature.

The life-saving process of clot production in response to an injury can become life-threatening when it occurs at inappropriate places in the body. For example, a clot can obstruct a blood vessel and stop the supply of blood to an organ or other body part. In addition, the deposition of fibrinogen contributes to partial or complete stenosis of blood vessels, resulting in chronic diminution of blood flow. Equally life-threatening are clots that become detached from their original sites and flow through the circulatory system causing blockages at remote sites. Such clots are known as embolisms. Indeed, pathologies of blood coagulation, such as heart attacks, myocardial infarctions, strokes, and the like, have been estimated to account for approximately fifty percent of all hospital deaths.

Fibrinogen is synthesized and secreted into the circulation by the liver. Circulating fibrinogen is polymerized under attack by thrombin to form fibrin, which is the major component of blood clots or thrombi. Subsequently, fibrin is depolymerized under attack by plasmin to restore the fluidity of the plasma. Many of the steps in the polymerization and depolymerization processes have been well established, Doolittle et al., *Annu. Rev. Biochem.*, 53:195–229 (1984). The elevated levels of fibrinogen which are part of the acute phase response occurring in the wake of infections and trauma are now known to come from increased hepatic production, primarily in response to interleukin-6 (IL-6). Seghal et al., *Ann N.Y. Acad. Sci.* 557:1–583.

Fibrinogen, one of the more well-studied proteins, plays a central role in clot formation and wound healing. It has a complex structure which includes a heavily disulfide-bonded hexamer composed of two copies each of the α, β and γ subunits. Recently, new attention has been given to structure/function relationships in the fibrinogen molecule. This new interest has in part been prompted by growth in the understanding of this protein's range of activity in normal and pathological states, see for example, Blomback et al., Biotechnology of Blood, 225–279 (1991), Bini et al., *Ann N.Y Acad. Sci.*, 667:112–126 (1992) and Dvorak et al., *Ann N.Y. Acad. Sci.*, 667:101–111 (1992).

By the late 1960's, the general subunit structure of fibrinogen was firmly established. Blomback et al., *Nature* 218:130–134. A decade later, the complete amino acid sequence was reported. Lottspeich et al., *Hoppe-Seyler's, Physiol. Chem.* 358:935–938 (1997), Henschen et al., *Hoppe-Seyler's, Physiol Chem.*, 358:1643–1646, Henschen et al., *Hoppe-Seyler's, Physiol Chem.*, 360:1951–1956, Doolittle et al., *Nature*, 280:464–468 (1979). Over the next 10 years, the cluster of three separate genes encoding the α (alpha), β (beta) and γ (gamma) subunits was identified on chromosome 4q23-q32, Kant et al., *Proc. Natl. Acad. Sci. USA*, 82:2344–2348 (1985), and the apparently complete genetic sequences of all three fibrinogen subunits were published. Chung et al., *Adv. Exp. Med. Biol.*, 281:39–48 (1991). These studies indicated that the a subunit lacked a globular C-terminal domain comparable to those present in the β and γ subunits.

The subsequent discovery of an additional exon (i.e., exon VI) downstream from the established a subunit gene has resolved the evolutionary mystery posed by the imperfectly parallel structure of the three major subunits. Fu et al., *Biochemistry*, 31:11968–11972 (1992), Weissbach et al., *Proc. Natl. Acad. Sci. USA*, 87:5198–5202 (1990). A novel fibrinogen α chain transcript has been identified at low frequency bearing the exon VI-derived sequences as a separate open reading frame. Additional splicing leads to the use of this extra sequence to elongate the α chain by 35% (236 similar to those of the β and γ chains.

A major impetus to fibrinogen research has been provided by the recent identification of this long overlooked, naturally occurring elongated version of the α subunit, designated "$\alpha_E$". See Fu et al., *Biochemistry*, 31:11968–11972 (1992). Evidence shows that the $\alpha_E$ chain is assembled into fibrinogen molecules and that its synthesis is enhanced by interleukin-6 (IL-6). These facts suggest that the $\alpha_E$ subunit participates in both the acute phase response and in normal physiology.

Using a polyclonal rabbit antibody preparation specific to the VI-domain or $\alpha_E C$ domain, $\alpha_E$ was demonstrated to occur in plasma fibrinogen as part of $(\alpha E \beta \gamma)_2$, a homodimeric (i.e., symmetrical) molecule of 420 kilodaltons (kDa). Fu et al., *Proc. Natl. Acad. Sci. USA*, 91:2625–2628 (1994). This species has been designated "fibrinogen-420" $(\alpha_E \beta \gamma)_2$ to distinguish it from the abundant 340 kDa form of fibrinogen, denoted "fibrinogen-340"$(\alpha \beta \gamma)_2$. Fibrinogen-420 accounts for approximately 1% of the total fibrinogen in normal adult plasma and 3% of the total in umbilical cord plasma. Grieninger et al., *Blood*, 90:2609 (1997). The relatively low circulating level of fibrinogen-420 is undoubtedly responsible for its having escaped detection. These two $\alpha_E C$ domains that distinguish Fibrinogen-420 from Fibrinogen-340 are likely to significantly influence the fibrinogen molecule's multiple binding capacities and functions.

Transcripts encoding fibrinogen subunit counterparts having exceptionally high C-terminal homology to human $\alpha_E$ have been detected thus far in lamprey, where it arises from a second α gene, as well as in chicken, rabbit, rat, and baboon. See Pan et al., *Proc. Natl. Acad. Sci. USA*, 89:2066–2070 (1992), Doolittle et al., *Thromb. Res.*, 68:489–493 (1992) and Fu et al., *Genomics* 30:71–76 (1995). This degree of α subunit-associated globular domain preservation in the vertebrate genome signals an important, if as yet unknown, role for $\alpha_E$. Clues to its potential significance may lie in the similarity of the extension in $\alpha_E$, not only to the corresponding regions of the fibrinogen and chains, but also to carboxy domains of a number of non-fibrinogen proteins from fruit fly to man. Chung et al., *Biochemistry*, 22:3244–3250 (1983), Chung et al., *Biochemistry* 22:3250–3256 (1983), Baker et al., *Science* 250:1370–1377 (1990), Koyama et al., *Proc. Natl. Acad. Sci. USA*, 84:1609–1613 (1987), Morel et al., *Proc. Natl. Acad. Sci. USA*, 86:6582–6586 (1989), Nies et al., *J. Biol. Chem.*, 266:2818–2823 (1991), Norenberg et al., *Neuron*, 8:849–863 (1992), Xu et al., *Proc. Natl. Acad. Sci. USA*, 87:2097–2101. Where functions are known, these non-fibrinogen proteins are constituents of the extracellular matrix and have adhesive properties. It is expected that continued research will permit the determination of whether the $\alpha_E$ globular domain contributes in a subtle way to the primary function of fibrinogen (clot formation and wound healing) or, following the example of other differentially used exons, promotes an alternative function. Chan et al., *Science*, 254:1382–1385 (1991), Descombes et al., *Cell*, 67:569–579 (1991), Early et al., *Cell*, 20:313–319 (1980). Thus there is a need to isolate fragments of the Fibrinogen-420 molecule.

In clinical settings it is commonly desirable to activate or potentiate the fibrinolytic system. This is particularly necessary in cases of myocardial infarction in which coronary arteries become occluded and require recanalization. Catheterization has proven somewhat effective in such recanalization, but pharmacologic agents are desired to supplement or replace such invasive procedures to inhibit reocclusion. The study of the intricate system of thrombolysis and fibrinolysis has been a rapidly growing field, which has resulted in the development of a new generation of thrombolytic agents.

Previous therapeutic treatments for dissolving life-threatening clots have included injecting into the blood system various enzymes which are known to break down fibrin. Collen D, *Circulation*, 93:857–865 (1996). The problems with these treatments has been that the enzymes were not site-specific, and, therefore, would do more than just cause dissolution of the clot. In addition, these enzymes interfere with and destroy many vital protein interactions that serve to keep the body from bleeding excessively due to the many minor injuries it receives on a daily basis. Destruction of these safeguards by such enzymes can lead to serious hemorrhage and other potentially fatal complications.

Currently, the best known therapeutic agents for inducing or enhancing thrombolysis are compounds which cause the activation of plasminogen, the so-called "plasminogen activators," Brakman et al., *Ann NY Acad Sci, vol. 667* (1992). These compounds cause the hydrolysis of the arg560-val561 peptide bond in plasminogen. This hydrolysis yields the active two-chain serine protease, plasmin. Both plasmin and plasminogen activator are produced endogenously in a mammal. A number of such plasminogen activators are known, including serine proteases such as urokinase plasminogen activator (u-PA), tissue-type plasminogen activator (t-PA), streptokinase (a non-enzyme protein) and staphylokinase. Of these, streptokinase is the most widely used therapeutic thrombolytic agent. However, while streptokinase and the other plasminogen activators have proven helpful in recanalization of coronary arteries, their ability to improve mortality is not devoid of side effects and their use still requires stringent control conditions to achieve success in a high percentage of cases, Martin et al., Chapter 72 in Hemostasis and Thrombisis: Basic Principles and Clinical Practice, 3rd ed., (1994). In addition, the use of such compounds can cause bleeding complications in susceptible individuals.

Elevated levels of fibrinogen have been found in patients suffering from clinically overt coronary heart disease, stroke and peripheral vascular disease. Although the underlying mechanisms remain speculative, recent epidemiological studies leave little doubt that plasma fibrinogen levels are an independent cardiovascular risk factor possessing predictive power which is at least as high as that of other accepted risk factors such as smoking, hypertension, hyperlipoproteinemia or diabetes. Ernst et al., J. Internal Med., 227:365–372 (1990), Ernst et al., Ann Intern. Med. 118:956–963 (1993).

During myocardial infarctions (M.I.) certain blood isoenzymes including CK (Creatine Phosphokinase)-MB (Muscle-Brain) are used to confirm the diagnosis of a M.I. in a subject as well as other parameters like electrocardiograms (ECG). These enzymes are often elevated, and must be monitored carefully for more than 72 hours. Treatment will be continued for this time or longer until a definitive diagnosis can be made. Thus, new methods are needed to accurately confirm suspected myocardial infarctions.

The structure of fibrin has been analyzed extensively in vitro by Doolittle et al., *Annu Rev Biochem* 53:195–229 (1984). Only recently, however, has attention been paid to the molecular structure of human thrombi and atherosclerotic plaques with respect to fibrinogen and fibrin products, Bini et al., *Blood* 69:1038–1045 (1987). Whereas thrombi formed in vivo consist primarily of fibrin II cross-linked by factor XIIIa, fibrinogen itself is a major component of uncomplicated atherosclerotic lesions, particularly fibrous and fatty plaques. Immunohistochemical as well as immunoelectrophoretic analyses indicate that fibrinogen in the aortic intima is comparatively well protected from thrombin and plasmin, and that much of it is deposited through direct cross-linking by tissue transglutaminase without becoming converted to fibrin, Valenzuela et al., *Am. J Pathol.* 141:861–880 (1992). Further understanding of these issues awaits the development of methods for the differential determination of fibrinogen subtypes in medical samples.

In wound repair, fibrinogen serves as a key protein, achieving rapid arrest of bleeding following vessel injury. It promotes both the aggregation of activated platelets with one another to form a hemostatic plug, as well as endothelial cell binding at the site of injury to seal the margins of the wound. As the most abundant adhesive protein in the blood, fibrinogen attaches specifically to platelets, endothelial cells and neutrophils via different integrins, Hynes et al., Cell, 69:11–25 (1992). Five putative receptor recognition domains on human fibrinogen, distributed over its three subunits, have been identified by in vitro and in vivo analyses. Kloczewiak et al., Biochemistry 23:1767–1774 (1984), Cheresh et al., Cell, 58:945–953 (1989), Loike et al., Proc Natl Acad Sci USA, 88:1044–1048 (1991), Farrell et al., Proc Natl Acad Sci USA, 89:10729–10732 (1992), Gonda et al., Proc Natl Acad Sci USA, 79:4565–4569 (1982), Ribes et al., J. Clin Invest., 84:435–442 (1989). In fibrinogen which contains the variant $\alpha_E$ chains, masking of these sites, as well as addition of new sites, are distinct possibilities with ramifications that must be explored.

As a result of the foregoing, there exists a need for a better understanding of the structure and function of fibrinogen, especially in relation to the fibrinogen-420$\alpha_E$ C domain. There also exists a need for isolating and purifying fragments of fibrinogen-420$\alpha_E$ C. Diagnosis and treatment of disease states associated with physiological processes involving fibrinogen-420 and fibrin-420 are lacking. The present invention effectively addresses these and other needs for the first time.

SUMMARY OF THE INVENTION

This invention relates to a diagnostic method, for characterizing fibrinogen, the method includes analyzing a sample, such as biological fluids and tissue, for $\alpha_E$CX fragments. Such analysis typically includes contacting the sample with at least one monospecific antibody that binds to an $\alpha_E$ C domain where specific binding of the antibody indicates the presence of the $\alpha_E$CX cleavage fragments of fibrinogen. These $\alpha_E$CX cleavage fragments of fibrinogen are defined by the amino acid sequence set forth in SEQ ID NO: 1, SEQ ID NO: 2, SEQ ID NO: 3 or homologs having at least 90% identity with SEQ ID NO: 2 in the sample. Presence of $\alpha_E$CX cleavage fragments indicates proteolytic degradation of fibrinogen-420, in vivo or in vitro and can be used to diagnose a myocardial infarction in a mammal. The diagnostic method of the present invention can also be used to regulate the amount of plasminogen activator or plasmin given to a mammal in vivo. In one preferred embodiment, the monospecific antibody that binds to an $\alpha_E$C domain of fibrinogen can further be detectably labeled with a detectable marker moiety. In another exemplary embodiment, the proteolytic enzyme includes plasminogen, plasminogen activator, fibrinolytic metalloproteinases, u-PA, t-PA, r-PA, n-PA, streptokinase, staphylokinase and combinations thereof.

The present invention also provides fibrinogen cleavage fragments, Fibrinogen-420$\alpha_E$CX fragments. These $\alpha_E$CX cleavage fragments of fibrinogen include amino acid sequences set forth in SEQ ID NO: 1, SEQ ID NO: 2, SEQ ID NO: 3 or homologs having at least 90% identity with SEQ ID NO: 2.

The invention also provides $\alpha_E$CX cleavage fragments of amino acid sequences set forth in SEQ ID NO: 1, SEQ ID NO: 2, SEQ ID NO: 3 or homologs having at least 90% identity with SEQ ID NO: 2, conjugated to a carrier for administration to a subject.

In one embodiment of the invention, $\alpha_E$CX cleavage fragments of amino acid sequences set forth in SEQ ID NO: 1, SEQ ID NO: 2, SEQ ID NO: 3 or homologs having at least 90% identity with SEQ ID NO: 2, are admixed with a physiologically acceptable diluent.

The invention further relates to a method of purifying $\alpha_E$CX fragments of fibrinogen-420 which includes contacting fibrinogen with a proteolytic enzyme to provide fragments of the fibrinogen, and selectively removing the $\alpha_E$CX cleavage fragments of fibrinogen defined by the amino acid sequence set forth in SEQ ID NO: 1, SEQ ID NO: 2, SEQ ID NO: 3 or homologs having at least 90% identity with SEQ ID NO: 2 from the sample.

In one preferred embodiment, the proteolytic enzyme can be fibrinolytic matrix metalloproteinase, plasmin, plasminogen activator u-PA, t-PA, r-PA, n-PA, streptokinase, staphylokinase an combinations thereof. The method of the present invention can also be performed in vitro or in vivo.

The invention further relates to a method of purifying fibrinogen which includes contacting fibrinogen with a proteolytic enzyme to provide fragments of the fibrinogen, contacting the fibrinogen fragments with at least one monospecific antibody that binds to an $\alpha_E$C domain of fibrinogen where specific binding of the antibody indicates the presence of the $\alpha_E$CX cleavage fragments of fibrinogen-420 and selectively removing the $\alpha_E$CX cleavage fragments of fibrinogen defined by the amino acid sequence set forth in SEQ ID NO: 1, SEQ ID NO: 2, SEQ ID NO: 3 or homologs having at least 90% identity with SEQ ID NO: 2 from the sample.

The present invention can also be used to detect $\alpha_E$CX fragments in vivo or in vitro. This method includes contacting fibrinogen with plasmin or a plasminogen activator to provide fragments of the fibrinogen, then contacting the fragments of fibrinogen with at least one monospecific antibody that binds to an $\alpha_E$C domain of fibrinogen, where specific binding of the antibody indicates the presence of the $\alpha_E$CX cleavage fragments of fibrinogen defined by the amino acid sequence set forth in SEQ ID NO: 1, SEQ ID NO: 2, SEQ ID NO: 3 or homologs having at least 90% identity with SEQ ID NO: 2 in the sample.

In one preferred embodiment, the monospecific antibody that binds to an $\alpha_E$C domain of fibrinogen can further be detectably labeled with a detectable marker moiety. In another preferred embodiment, the present invention can also be used to detect $\alpha_E$CX fragments in vivo, for example, in a mammal suffering from a myocardial infarction. The presence of $\alpha_E$CX cleavage fragments in a sample of blood indicates that fibrin(ogen)olysis has occurred.

In yet another embodiment of the invention, a monospecific antibody is provided which binds with an epitope of the $\alpha_E$CX cleavage fragment of fibrinogen. This monospecific antibody can be monoclonal. Preferably such antibodies can be labeled with a detectable moiety such as radioactive labels, enzymes, specific binding pair components, colloidal dye substances, fluorochromes, reducing substances, latexes, digoxigenin, metals, particulates, dansyl lysine, antibodies, protein A, protein G, electron dense materials, chromophores, affinity columns and the like.

In another embodiment of the invention, a nucleic acid comprising nucleotide SEQ ID NO: 5, is provided. This nucleic acid encodes $\alpha_E$CX cleavage fragments set forth in: SEQ ID NO: 1, SEQ ID NO: 2, SEQ ID NO: 3, or homologs having at least about 90% identity with SEQ ID NO: 2. The nucleic acid can be isolated, natural or synthetic DNA or RNA encoding SEQ ID NO: 1, SEQ ID NO: 2, SEQ ID NO: 3, or a homolog having at least about 90% identity with SEQ ID NO:2.

The invention also includes a vector for transfecting a host cell to express heterologous or recombinant proteins including the DNA segment encoding SEQ ID NO: 1, SEQ ID NO: 2, SEQ ID NO: 3, or homologs having at least about 90% identity with SEQ ID NO: 2, which is conjugated to a promoter.

The method of the present invention includes a method of making a host cell which expresses a heterologous or recombinant protein which includes transfecting the cell with a vector including a DNA segment encoding SEQ ID NO: 1, SEQ ID NO: 2, SEQ ID NO: 3, or homologs having at least about 90% identity with SEQ ID NO:2, conjugated to the promoter.

Still another embodiment of the present invention is a method for treating a mammal suffering from conditions or pathologies related to fibrinogen metabolism by administering an effective amount of a composition which includes SEQ ID NO: 1, SEQ ID NO: 2, SEQ ID NO: 3, or homologs having at least 90% identity with SEQ ID NO:2.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein.

DETAILED DESCRIPTION OF THE INVENTION

Figure 1:
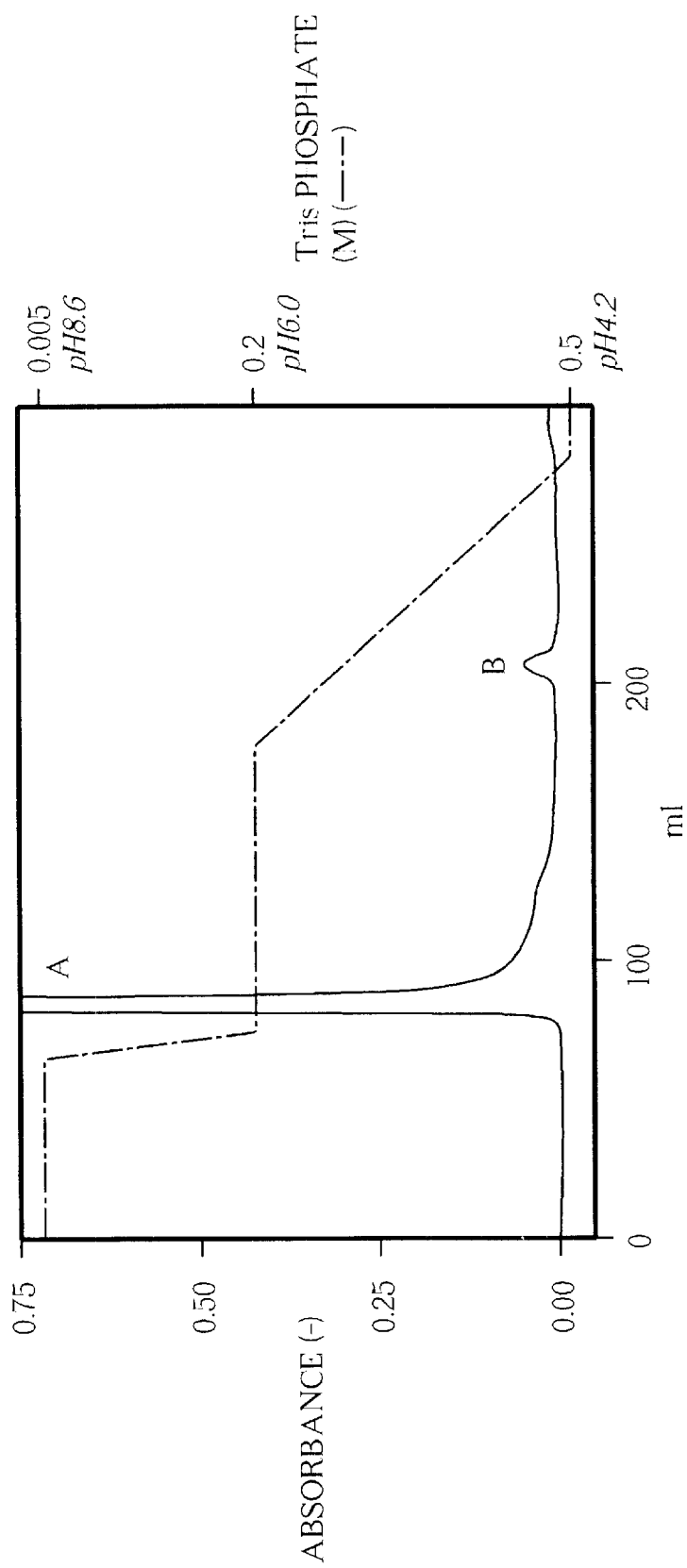
FIG. 1 is a graphic illustration of the separation of fibrinogen species by Mono Q anion exchange chromatography. Human fibrinogen (fraction I-2) was purified from umbilical cord plasma and then subjected to column chromatography as described in Materials and Methods. The elution profile is plotted with absorbance at 280 nm as a solid line (scale on the left) and the step-wise gradient in Tris Phosphate (In all Tris Phosphate buffers, the molarity refers to phosphate (Mosesson et al., *Biochemistry* 247:5223 (1972)) is indicated by the broken line (scale on the right). The major and minor peaks are labeled "A" and "B", respectively.

It has now been discovered that these and other objectives can be achieved by the present invention, which provides novel α$_E$CX cleavage fragments of fibrinogen. The novel α$_E$CX cleavage fragments of fibrinogen have the amino acid sequence set forth in SEQ ID NO: 1, SEQ ID NO:2, SEQ ID NO:3, or are homologs having 90% homology with SEQ ID NO:2.

For purposes of more clearly and accurately describing the invention herein, certain terminological conventions have been adopted in the following discussion. These conventions are intended to provide a practical means for enhancing description of the invention, but are not intended to be limiting, and the skilled artisan will appreciate that other and additional, albeit not inconsistent, interpretations can be implied.

The term "fibrinogen" without more is intended to include any type of fibrinogen. Fibrinogen, therefore, refers to monomeric and dimeric fibrinogen molecules having the monomer structure (αβγ), as well as molecules having the monomer structure (α$_E$βγ), and other hybrid molecules, whether naturally occurring, modified, or synthetic. The term "fibrinogen" refers generally to fibrinogen from humans but may include fibrinogen of any species. In addition, the term may be specifically limited to a particular species in particular contexts, such as "human fibrinogen."

Fragments of fibrinogen refer to the less than the complete amino acid structure of fibrinogen. When fibrinogen is subjected to proteolytic attack by plasmin, or plasminogen activator or fibrinolytic metalloproteinase, in vivo or in vitro, certain fibrinogen cleavage fragments are formed. Knowledge of the conventional fragmentation of fibrinogen assists in providing a conceptual framework against which to compare the activity of other potential fibrinolytic enzymes. It is known that, due to the fluidity and complexity of the physiology of fibrinogen formation and degradation, many forms of fibrinogen are present in the circulating blood as well as in thrombotic and atherosclerotic lesions. The many forms of these molecules result from continual assault by proteolytic enzymes which variously cleave the molecules.

The term "fibrinolytic state" refers to the status of fibrinolytic system in a mammal. It is an indicator of the fibrinolytic system which is responsible for fibrin breakdown and clot removal in vivo. Action of the fibrinolytic system is tightly coordinated through the interaction of activators, zymogens, enzymes, as well as through inhibitors of each of these components, to provide focused local activation at sites of fibrin deposition.

The term "Fibrinogen-340" refers to the predominant subclass of human fibrinogen, which molecules have the homodimeric structure (αβγ)$_2$, and have a molecular weight of 340 kilodaltons (kDa) or less. A range of molecular weights of fibrinogen with a maximum of about 340 kDa is normally observed, and is attributed to variations in the lengths of the a subunit tails due to their having been subjected to various amounts of proteolytic cleavage.

The term "Fibrinogen-420" refers to the minor subclass of human fibrinogen, which molecules have the homodimeric structure $(\alpha_E\beta\gamma)_2$, and have a molecular weight of about 420 kDa. See Fu et al., *Proc. Natl. Acad. Sci. USA*, 91:2625–2628 (1994). In normal subjects, this type of fibrinogen occurs with a frequency of about 1% of all fibrinogen in the body. This type of fibrinogen generally does not exhibit much variance in molecular weight, probably because the a subunit tail may be substantially protected from random proteolytic attack by virtue of the presence of the additional globular domain peculiar to the $\alpha_E$ subunit. The term" $\alpha_E$ subunit" refers to the 847 amino acid sequence set forth in SEQ ID NO. 4 on the Fibrinogen-420 molecule.

For the purposes of the present invention, the term "monospecific antibody" most commonly refers to a monoclonal antibody, also abbreviated "MoAb", as that term is conventionally understood. The term "monospecific antibody" as used herein may, however, refer to homogeneous antibodies which are native, modified, or synthetic, and can include hybrid or chimeric antibodies. The term does not include "polyclonal antibodies" as that term is commonly understood.

The term "isolated" as used herein, refers to $\alpha_E$CX fragments which are unaccompanied by at least some of the material with which it is associated in its natural state, preferably constituting at least 0.5% by weight of the total protein in a given sample, more preferably at least 5% by weight of the total protein in a given sample, and most preferably the "isolated" protein is substantially free of other proteins, lipids, carbohydrates or other materials which it is naturally associated.

Proteolytic enzymes that are known to cleave, digest, or degrade fibrinogen according to the present invention include fibrinolytic matrix metalloproteinase, plasmin, plasminogen activator, which includes u-PA, t-PA, r-PA, n-PA, streptokinase, staphylokinase and combinations thereof. These enzymes can be added by exogenous administration to a mammal or can be produced endogenously in vivo by the mammal. For the present invention, mammals include humans and other primates, as well as pet animals such as dogs and cats, laboratory animals such as rats and mice, and farm animals such as horses, sheep, and cows. Proteolytic enzymes can also be added to a testable system which include in vivo or in vitro testable systems, and combinations thereof In vitro for purposes of the present invention includes cellular systems.

It is known that initial cleavages of fibrinogen liberates the carboxy-terminal, polar appendage of the Aα chain, and a peptide from the N-terminal portion of the Bβ chain (Bβ1–42). The remaining major fragment is Fragment X. Cleavages of all three polypeptide chains along one coiled coil connecting the central N-terminal knot (E) and a terminal (D) domain of fragment X split it asymmetrically. The result is one fragment D molecule, which consists of carboxy-terminal portions of the three chains, and a fragment Y moiety, consisting of central and terminal domains still connected by a coiled coil. Subsequent cleavage of the coiled coil of fragment Y produces a second fragment D and a fragment E moiety. Fragment X is slowly coagulable by thrombin, but fragments Y and D have potent antipolymerizing effects, due mostly to disruption of the proper alignment and continuation of build-up of the protofibrils of fibrin.

In addition to the known cleavages of fibrinogen, Applicants have found that these proteolytic enzymes cleave, digest, or degrade the Fibrinogen-420 subunit on the fibrinogen molecule cleaving the $\alpha_E$C domain from the Fibrinogen-420 subunit resulting in plasmin degradation products designated herein as "$\alpha_E$CX" fragments. The "$\alpha_E$CX" fragment includes compositions of matter, which compositions comprise a band having an apparent molecular weight of from about 34 to about 40 kilodaltons as determined by denaturing, non-reducing polyacrylamide gel electrophoresis. Such compositions or fragments detected by a monospecific antibody directed to $\alpha_E$ C domain of fibrinogen. The $\alpha_E$ CX fragment co-migrates with the 34 kDa yeast recombinant $\alpha_E$ C domain when the relative molecular mass is determined on denaturing, non-reducing polyacrylamide gel electrophoresis.

Accordingly, Applicants have been the first to isolate, cleave and identify $\alpha_E$CX fragments from the Fibrinogen-420$\alpha_E$C chain. Fragments $\alpha_E$ CX isolated in the present invention comprise amino acid sequence set forth in SEQ ID NO:1, SEQ ID NO:2, SEQ ID NO:3, and includes homologs having about 90% identity with SEQ ID NO:2.

Determination of whether two amino acid sequences are homologs are, for the purpose of the present specification, based on FASTA searches in accordance with Pearson et al., *Proc. Natl. Acad. Sci. USA*, 85:2444–2448 (1988). A substantially homologous $\alpha_E$CX fragment sequence in accordance with the present invention is preferably at least about 65% identical to SEQ ID NO:2. In the case of fragments having high homology, the amino acid sequence of the first fragment is at least about 75% identical, preferably at least about 85% identical, and most preferably at least about 90% identical to the amino acid set forth in SEQ ID NO:2.

As is also known, it is possible to substitute amino acids in a sequence with equivalent amino acids. Groups of amino acids known normally to be equivalent are:
(a) Ala (A), Ser (S), Thr (T), Pro (P), Gly (G);
(b) Asn (N), Asp (D), Glu (E), Gln (Q);
(c) His (H), Arg (R), Lys (K);
(d) Met (M), Leu (L), Ile (I), Val (V); and
(e) Phe (F), Tyr (Y), Trp (W).

Substitutions, additions, and/or deletions in the sequences may be made as long as the fragments of the invention continue to be functionally identical by exhibiting similar binding of a ligand.

For example, the $\alpha_E$ domain or chain of the Fibrinogen-420 set forth in SEQ ID NO:4, includes the $\alpha_E$C portion that is defined as amino acids from 612–847 starting with Aspartic Acid represented by the single letter code D at the 612 position. The $\alpha_E$C domain consists of 236 amino acids, when this site is cleaved (the peptide bond between R and D is broken), degraded or digested by plasmin from fibrinogen-420, the resulting fragment is $\alpha_E$CX fragment which is set forth in SEQ ID NO:2. Since plasmin may cleave fibrinogen-420 at different sites, there are resulting fragments such as those set forth in SEQ ID NO:1, SEQ ID NO:3 which may be similar or identical with SEQ ID NO:2 by about 90%. Thus, other substitutions and deletions and possibly additions to the amino acid sequence are contemplated by the present invention.

$\alpha_E$CX cleavage fragments of the present invention have been found to have prolonged stability. As used herein, prolonged stability means the fragments have been found to remain molecularly intact under physiological conditions in vivo and in vitro for up to about 24 hours after isolation.

Fibrinogen fragments of the present invention set forth in SEQ ID NO:1, SEQ ID NO:2, SEQ ID NO:3 or homologs having at least about 90% identity with SEQ ID NO:2 can be attached to a pharmaceutically acceptable carrier. These carriers are well known in the art and include solvents, salts, excipients, physiological substances, bulking agents, and the like. In addition, other components which are separately reactive with fibrinogen, such as other monoclonal or polyclonal antibodies, receptive molecules, or fibrinogen binding portions thereof maybe included as acceptable carriers.

Preferably, the $\alpha_E$CX fragments of the present invention set forth in SEQ ID NO:1, SEQ ID NO:2, SEQ ID NO:3 or homologs having at least about 90% identity with SEQ ID NO:2, can be placed in a physiologically acceptable diluent (medium), e.g. phosphate buffered saline, optionally containing an adjuvant. The $\alpha_E$CX fragments with adjuvant can be administered to a mammal by methods known to those skilled in the art. For example, the subcutaneous, intravenous, intradermal or intramuscular routes can be employed. Generally speaking, the amount of the fragment that can be placed in physiologically acceptable diluent or in carriers can be between approximately 1 $\mu$g to 1 mg per dose.

As used herein, "precursor $\alpha_E$ CX fragments" include a composition of matter, which composition comprises a band having an apparent molecular weight of from about 36 to about 80 kilodaltons as determined by denaturing, non-reducing polyacrylamide gel electrophoresis. Such composition is detected by a monospecific antibody directed to $\alpha_E$ C domain of fibrinogen. Such precursor $\alpha_E$ CX fragments have slower mobility as compared to the 34 kDa yeast recombinant $\alpha_E$ C domain when the relative molecular mass is determined on denaturing, non-reducing polyacrylamide gel electrophoresis. Precursor $\alpha_E$ C fragments of fibrinogen include cleavage products of fibrinogen-420 that contain the $\alpha$C tether. Such $\alpha$C tether is disclosed in Fu et al., *Blood*, 92:3302–3308,1998, the entire disclosure is incorporated by reference.

The present invention also provides a method for treating a mammal suffering from conditions associated with fibrinogen metabolism comprising administering to said mammals an effective amount of a composition comprising SEQ ID NO:1, SEQ ID NO:2, SEQ ID NO:3 or homologs having at least about 90% identity with SEQ ID NO:2. The composition may also be conjugated to a carrier.

As used herein, fibrinogen metabolism includes fibrinogenesis or the production or formation of fibrin(ogen) in the blood via the action of thrombin. Fibrinogen metabolism also includes abnormal fibrinolysis or the dissolution of fibrin(ogen) in blood clots chiefly by proteolytic enzymes, such as for example, plasmin or streptokinase.

Conditions known to be associated with fibrinogen pathology or metabolism include trauma, generating the need for wound repair, angiogenesis, and cancer as well as other conditions.

An effective amount as used herein is that amount of the composition comprising SEQ ID NO:1, SEQ ID NO:2, SEQ ID NO:3 or homologs having at least about 90% identity with SEQ ID NO:2, effective to achieve the specified result of treating conditions characterized by fibrinogen metabolism.

One aspect of the present invention includes a method for detecting Fibrinogen-420 $\alpha_E$CX fragments by contacting fibrinogen fragments with at least one monospecific antibody that binds to an $\alpha_E$C domain of fibrinogen where specific binding of the antibody indicates the presence of the $\alpha_E$CX cleavage fragments of fibrinogen defined by SEQ ID NO:1, SEQ ID NO:2, SEQ ID NO:3 or homologs having at least about 90% identity with SEQ ID NO:2.

The sample containing the fibrinogen or fibrinogen fragments can be any biological fluid including blood, urine, sputum, cerebral spinal fluid or other physiological fluid.

In the methods of the present invention, plasmin or plasminogen activator may be produced endogenously in vivo, by the mammal in response to clot formation or atherogenesis. Endogenous production of plasmin or plasminogen activator will cause circulating fibrinogen to be cleaved resulting in fibrinogen fragments, in which case contacting fibrinogen with exogenous plasmin or plasminogen activator may or may not be necessary because this has been done endogenously within the mammal.

These fibrinogen fragments are contacted with monoclonal antibodies MoAb produced by hybridoma cell lines identified as #3-10, #29-1 and #148-B. Such antibodies are specific for the $\alpha_E$C domain unique to $\alpha_E$ chain. These antibodies are disclosed in U.S. patent application Ser. No. 08/479,775, filed on Jun. 7, 1995, the entire disclosure of which is incorporated herein by reference. Preferably, the method is performed using conditions which are conducive to binding of fibrinogen with the monoclonal antibodies.

Antibodies of the present invention, can be detectably labeled by conjugation to a detectable moiety. Detectable moieties suitable for use in the present invention include radioactive labels, enzymes, specific binding pair components, colloidal dye substances, fluorochromes, reducing substances, latexes, digoxigenin, metals, particulates, dansyl lysine, antibodies, protein A, protein G, electron dense materials, chromophores, affinity columns and the like.

The present invention also includes a method of purifying Fibrinogen-420 $\alpha_E$CX fragments by optionally contacting a sample of fibrinogen with plasmin or a plasminogen activator to provide fragments of the fibrinogen, contacting the fragments of fibrinogen with at least one monospecific antibody that binds to an $\alpha_E$C domain of fibrinogen where specific binding of the antibody indicates the presence of $\alpha_E$CX cleavage fragments of fibrinogen and selectively removing the $\alpha_E$CX cleavage fragments of fibrinogen defined by the amino acid sequence set forth in SEQ ID NO:1, SEQ ID NO: 2, SEQ ID NO: 3 or homologs having at least 90% identity with SEQ ID NO: 2 in the sample.

In another embodiment of the invention the method includes purifying Fibrinogen-420 $\alpha_E$CX fragments by contacting the fragments of fibrinogen with at least one monospecific antibody that binds to an $\alpha_E$C domain of fibrinogen where specific binding of the antibody indicates the presence of $\alpha_E$CX cleavage fragments of fibrinogen and selectively removing the $\alpha_E$CX cleavage fragments of fibrinogen defined by the amino acid sequence set forth in SEQ ID NO:1, SEQ ID NO: 2, SEQ ID NO: 3 or homologs having at least 90% identity with SEQ ID NO: 2 in the sample.

The antibody bound fibrinogen with $\alpha_E$CX cleavage fragments defined by the amino acid sequence set forth in SEQ ID NO:1, SEQ ID NO:2, SEQ ID NO:3 or homologs having at least 90% identity with SEQ ID NO: 2, is removed from the sample. Removal may be accomplished by chromatography-type methods, both preparative and analytical. Numerous such methods are known in the art and can be selected by the artisan as desired. In this method, the $\alpha_E$CX cleavage fragments may be soluble, suspended in fluid phase, or attached to a substantially solid phase, as desired.

Preferably, $\alpha_E$CX cleavage fragments may be pure or purified, which means that the proteins are free not only of other proteins, but also of other materials used in the processes of isolation, identification, or purification of the proteins. Thus, the fragments are free of materials such as, for example, detergents, affinity binding agents and separation films. Detergents include sodium dodecyl sulfate and sarcosine. Affinity binding agents include agarose, avidin-agarose, streptavidin-agarose, biotin, and biotinylated proteins. Separation films include nitrocellulose paper and nitrocellulose/cellulose acetate paper. Fragments of the present invention are at least 90% free, preferably at least 95% free, and more preferably at least 98% free of such materials.

Mixtures of $\alpha_E$CX cleavage fragments can be separated by, for example, SDS-PAGE in accordance with the method of Laemmli, *Nature*, 227:680–685 (1970). The molecular weights are determined by resolving single bands on SDS-PAGE and comparing their positions to those of known standards.

The invention further includes a diagnostic method for determining a fibrinolytic state or atherogenesis state in a mammal, which includes contacting fragments of fibrinogen with at least one monospecific antibody that binds to an $\alpha_E$C domain of fibrinogen and measuring specific binding of the antibody to the $\alpha_E$CX cleavage fragments wherein specific binding of the antibody indicates the presence of $\alpha_E$CX cleavage fragments of fibrinogen defined by an amino acid sequence set forth in: SEQ ID NO:1, SEQ ID NO:2, SEQ ID NO:3 or homologs having at least about 90% identity with SEQ ID NO:2 in the sample.

Applicants have found that the presence of $\alpha_E$CX cleavage fragments indicates fibrinolysis (clot digestion or dissolution) or atherogenesis in vivo. Therefore, the present invention can be used to diagnose a myocardial infarction in a mammal. In another embodiment, the present invention can be used to diagnose reperfusion in the case of a myocardial infarction in a mammal.

As used herein, reperfusion includes restoration of blood flow to an organ or tissue. For example, after a myocardial infarction, an immediate goal is to quickly open blocked arteries and reperfuse the heart muscles. Early reperfusion minimizes the extent of heart muscle damage and preserves the pumping function of the heart.

Myocardial infarction (M.I.) include localized necrosis of the myocardium as a result of interruption of the blood supply to that area due to a thrombosis. Diagnosis of a myocardial infarction is based on certain laboratory findings such as, for example, electrocardiograms (ECG), blood iso-enzymes including CK (Creatine phosphokinase)-MB (Muscle-Brain), and other clinical presentations. Often treatment is started empirically when a myocardial infarction is suspected. Definitive diagnosis of an M.I. in a subject can be based on blood iso-enzymes being elevated. These enzymes must be monitored carefully for more than a seventy-two hour period. Treatment will be continued for this time or longer until a definitive diagnosis can be made. See Ryan et al., *J.A.C.C.* 28: 1341–1342 (1996), for a review of diagnosis and treatment of myocardial infarctions.

Using the diagnostic method of the present invention in vivo, a sample containing fibrinogen fragments is collected from a mammal suspected of having an M.I. Plasmin or plasminogen activator or other proteolytic enzyme may be produced endogenously in vivo, by the mammal in response to clot formation or atherogenesis. Endogenous production of plasmin or plasminogen activator or other proteolytic enzyme will cause circulating fibrinogen to be cleaved resulting in fibrinogen fragments, in which case contacting fibrinogen with exogenous plasmin or plasminogen activator or other proteolytic enzyme may or may not be necessary because this has been done endogenously within the mammal. Alternately, plasmin or plasminogen activator or other proteolytic enzymes may be administered exogenously, for example intravenously, to the mammal resulting in fragments of fibrinogen.

The fibrinogen fragments are then collected in a sample from the mammal, contacted with at least one monospecific antibody that binds to an $\alpha_E$C domain of fibrinogen. Specific binding of the antibody to the $\alpha_E$CX cleavage fragments are measured wherein specific binding of the antibody indicates the presence of $\alpha_E$CX cleavage fragments of fibrinogen defined by an amino acid sequence set forth in: SEQ ID NO:1, SEQ ID NO:2, SEQ ID NO:3 or homologs having at least about 90% identity with SEQ ID NO:2 in the sample. This indicates fibrinolysis or atherogenesis in vivo.

The method can also be used to regulate doses of plasminogen activator or plasmin or other proteolytic enzymes administered to a mammal in which case if there are no $\alpha_E$CX cleavage fragments of fibrinogen detected then the dose of plasminogen activator can be increased. Plasminogen activators for the present invention include fibrinolytic matrix metalloproteinase, u-PA, t-PA, r-PA, n-PA, streptokinase, staphylokinase, and combinations thereof.

The invention further provides a monospecific antibody which binds with an epitope of an $\alpha_E$CX cleavage fragment of fibrinogen. The monospecific antibody will bind to an antigen-binding region which refers to a naturally occurring, modified, or synthetic fragment of a monospecific antibody of the invention that is reactive with an epitope of the $\alpha_E$CX domain of fibrinogen. Such antigen-binding regions include, but are not limited to, Fab, F(ab')2, and Fv fragments.

Monospecific antibodies to the $\alpha_E$CX can be manufactured according to U.S. patent application Ser. No. 08/479,775, filed on Jun. 7, 1995, the entire disclosure of which is incorporated herein by reference. These antibodies can be detectably labeled by conjugation to a detectable moiety. Detectable moieties suitable for use in the present invention include radioactive labels, enzymes, specific binding pair components, colloidal dye substances, fluorochromes, reducing substances, latexes, digoxigenin, metals, particulates, dansyl lysine, antibodies, protein A, protein G, electron dense materials, chromophores, affinity columns and the like.

The present invention relates, in general, to a nucleic acid molecule set forth in SEQ ID NO:5, e.g., DNA or RNA, encoding $\alpha_E$CX cleavage fragments of fibrinogen defined by the amino acid sequence set forth in: SEQ ID NO:1, SEQ ID NO:2, SEQ ID NO:3 or homologs having at least about 90% identity with SEQ ID NO:2. Since the amino acid sequences of the $\alpha_E$CX cleavage fragments have been identified by the present invention, and the nucleic acid sequence encoding the $\alpha_E$ domain is known, one of ordinary skill in the art, given the present disclosure, could easily identify and clone the DNA and RNA sequences without undue experimentation.

The DNA encoding the fragment of the invention may be replicated and used to express recombinant protein following insertion into a wide variety of host cells in a wide variety of cloning and expression vectors. The host may be prokaryotic or eukaryotic. The DNA may be obtained from natural sources and, optionally, modified. The genes may also be synthesized in whole or in part.

In one embodiment, the invention relates to an isolated or synthetic DNA comprising the nucleotide sequence set forth in SEQ ID NO: 5, encoding $\alpha_E$CX cleavage fragments of fibrinogen defined by the amino acid sequence set forth in: SEQ ID NO:1, SEQ ID NO:2, SEQ ID NO:3 or homologs having at least about 90% identity with SEQ ID NO:2. The DNA segment can be genomic DNA or cDNA. Of course, given the known degeneracy of the genetic code, the DNA sequences of the invention include those which substitute other nucleotides in appropriate positions to encode the defined $\alpha_E$CX cleavage fragments of fibrinogen.

In another embodiment, using methodology well known in the art, the invention includes a messenger RNA (mRNA) molecule encoding $\alpha_E$CX cleavage fragments of fibrinogen defined by the amino acid sequence set forth in: SEQ ID NO:1, SEQ ID NO:2, SEQ ID NO:3 or homologs having at least about 90% identity with SEQ ID NO:2. In this embodiment, the invention includes both spliced and non-spliced mRNA encoding $\alpha_E$CX cleavage fragments of fibrinogen. This embodiment further includes naturally occurring variants of these mRNAs, including allelic forms, as well as mRNAs encoding $\alpha_E$CX cleavage fragments of fibrinogen within the constraints of the degeneracy of the genetic code.

Cloning vectors may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13 fd, and other filamentous single-stranded DNA phages.

Vectors for expressing proteins in bacteria, especially *E. coli*, are also known. Such vectors include the pK233 (or any of the tac family of plasmids), T7, pBluescript II, bacteriophage lamba ZAP, and lambda PL (Wu, R. (Ed.), Recombinant DNA Methodology II, *Methods Enzymol.*, Academic Press, Inc., New York (1995)). Examples of vectors that express fusion proteins are PATH vectors described by Dieckmann and Tzagoloff, *J. Biol. Chem.* 260:1513–1520 (1985). These vectors contain DNA sequences that encode anthranilate synthetase (TrpE) followed by a polylinker at the carboxy terminus. Other expression vector systems are based on beta-galactosidase (pEX); maltose binding protein (pMAL); glutathione S-transferase (pGST or pGEX)—see *Mol. Cell Biol.* 4:220 (1993); *Gene* 67:31 (1988) and *Peptide Research* 3:167 (1990); and TRX (thioredoxin) fusion protein (TRXFUS). See, for example, LaVallie, R. et al., *Bio/Technology* 11:187 (1993).

Vectors useful for cloning and expression in yeast are available. A suitable example is the 2 μm circle plasmid, Ycp50, Yep24, Yrp7, and pYAC3 (Ausubel, F. M. et al. (Eds.), *Current Protocols in Molecular Biology*, John Wiley & Sons, Inc., New York, (1999).

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e., shuttle vectors, allow for the isolation and identification of protein coding sequences in prokaryotes.

Further eukaryotic expression vectors are known in the art (e.g., P J Southern and P Berg, *J. Mol. Appl. Genet.* 1:327–341 (1982); Subramani et al. (1981); R J Kaufmann and P A Sharp, "Amplification and expression of sequences co-transfected with a modular dihydrofolate reductase complementary DNA gene," *J. Mol. Biol.* 159:601–621 (1982); R J Kaufmann and P A Sharp, *Mol. Cell Biol.* 159:601–664 (1982); SI Scahill et al., "Expression and characterization of the product of a human immune interferon DNA gene in Chinese hamster ovary cells," *Proc. Natl. Acad. Sci. USA*, 80:4654–4659 (1983); G Urlaub and L A Chasin, *Proc. Natl. Acad. Sci. USA*, 77:4216–4220 (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, the tet system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

The present invention provides a recombinant DNA molecule including nucleotide sequence set forth in SEQ ID NO: 5, comprising a vector and a DNA segment encoding $\alpha_E$CX cleavage fragments of fibrinogen defined by the amino acid sequence set forth in: SEQ ID NO:1, SEQ ID NO:2, SEQ ID NO:3 or homologs having at least about 90% identity with SEQ ID NO:2.

Using methodology well known in the art, recombinant DNA molecules of the present invention can be constructed, and numerous vectors, including eukaryotic and prokaryotic vectors are commercially (and otherwise) available to the artisan. The DNA segment encoding $\alpha_E$CX cleavage fragments of fibrinogen defined by the amino acid sequence set forth in: SEQ ID NO:1, SEQ ID NO:2, SEQ ID NO:3 or homologs having at least about 90% identity with SEQ ID NO:2 can be present in the vector operably linked to regulatory elements, including, for example, a promoter.

The invention further includes host cells comprising the above-described recombinant DNA molecule. The recombinant DNA molecule may be stably transformed, stably transfected, or transiently transfected into the host cells or infected into the host cells by a live attenuated virus. The host cells can be, for example, prokaryotic cells such as *Escherichia coli, Staphylococcus aureus, Pichia pastoris* or eukaryotic cells such as a yeast, e.g., *Saccharomyces cerevisiae*, or cultured cells from multicellular organisms, e.g., Chinese hamster ovary cells (CHO) or Cos cells.

The following examples are intended to assist in a further understanding of the invention. The particular materials and conditions employed are intended to be further illustrative of the invention and are not limiting upon the reasonable scope thereof.

EXAMPLES

The following experimental procedures are relevant to examples 1 and 2 below:

Materials:

Human umbilical cord plasma was donated through the Placental Blood Program of the New York Blood Center. Blood collection and plasma processing for these samples have been described elsewhere (Grieninger, G. et al., *Blood* 90:2609, 1997; Rubinstein, P. et al., *Proc. Natl. Acad. Sci. USA* 92:10119, 1995). Plasma samples from patients undergoing thrombolytic therapy with recombinant tissue plasminogen activator or streptokinase were generously provided by Columbia Presbyterian Medical Center, NY. The samples were archival, originating from The TIMI Study Group's Phase I Trial (The TIMI Study Group: The Thrombolysis in Myocardial Infarction (TIMI) Trial: Phase I Findings. *N. Engl. J. Med.* 312:932, 1985).

Human plasmin and α-thrombin were generous gifts of Sinai Samaritan Medical Center, Milwaukee, Wis. Recombinant factor XIII was graciously provided by ZymoGenetics, Seattle, Wash.

Rabbit anti-fibrinogen was purchased from DAKO Corporation (Carpenteria, Calif.). Rabbit anti-$\alpha_E$C #9395, also known as anti-VI, was generated against a recombinant human $\alpha_E$C domain expressed in *E. coli*; it has been described previously (Fu. Y. et al., *Biochemistry* 31:11968, 1992; Fu, Y. et al., *Proc. Natl. Acad. Sci. USA* 91:2625, 1994). Rabbit anti-αamino acids 615–625 of SEQ. ID NO.: 2 and SEQ. ID NO.: 4, a gift from University of California—San Diego, La Jolla, Calif., was generated against the synthetic peptide TSPLGKPSLSP (Seq. ID. No. 6) This sequence corresponds to the carboxyl-terminal residues of the α(amino acids 1–625 of SEQ. ID NO.: 4) chain (Rixon, M. W. et al., *Biochemistry* 22:3237, 1983; Kant, J. A. et al., *Proc. Natl. Acad. Sci. USA* 80:3953, 1983) before it is processed to the predominant plasma form a(amino acids 1–610 of SEQ. ID NO.: 4) (Doolittle, R. F. et al., *Nature* 280:464, 1979). On Western blots, the antibody reacted strongly with fibrinogen present in spent medium from HepG2 culture, obtained as described previously (Fu, Y. et al., *Proc. Natl. Acad. Sci. USA* 91:2625, 1994); these cells are known to secrete a significant proportion of α(amino acids 1–625 of SEQ. ID NO.: 4)-containing fibrinogen (Farrell, D. H. et al., *J. Biol. Chem.* 268:10351, 1993).

Mouse monoclonal anti-$\alpha_E$C #29-1 was also generated against a recombinant human $\alpha_E$C expressed in *E. coli* and is specific for an epitope at the domain's C-terminus (Applegate, D. et al., *Blood* 92:3669, 1998). Monoclonal anti-α(amino acids of 603–610 SEQ. ID NO.: 4) antibody, F-48, kindly provided by Bristol-Myers Squibb, Princeton, N.J., was generated against the synthetic octapeptide, GHAKSRPV (Seq. ID No. 7) representing the common α chain carboxyl terminus; it is specific for processed but non-degraded α chains in plasma fibrinogen (Rudchenko, S. et al., *J. Biol. Chem.* 271:2523, 1996). Monoclonal anti-α chain antibody, 1D4, supplied by Bohdan Kudryk, has been described previously (Procyk, R. et al., *Biochemistry* 31:2273, 1992).

Column Chromatography:

Human fibrinogen (fraction I-2) was prepared from umbilical cord plasma according to Mosesson and Sherry (Mosesson, M. W. et al., *Biochemistry* 5:2829, 1966) and dialyzed against 0.005 M Tris Phosphate, pH 8.6. In all Tris Phosphate buffers, the molarity refers to phosphate (Mosesson et al., *Biochemistry* 247:5223 (1972). The material (30 ml at a concentration of 4 mg/ml) was applied to a Mono Q HR 10/10 anion exchange column (Pharmacia, Piscataway, N.J.) that previously had been equilibrated with the same buffer. Bound protein was eluted using a step-wise gradient starting from 0.005 M Tris Phospate, pH 8.6 to a final 0.5 M Tris Phosphate, pH 4.2. Eluted protein was collected in 2.5-ml fractions. For storage and further analysis, pooled fractions were either dialyzed against 125 mM NaCl, 25 mM HEPES (pH 7.4) or concentrated and exchanged to the buffer using a YM10 ultrafiltration membrane within an Amicon stirred cell (Amicon Inc, Beverly, Mass.).

SDS-PAGE and Western Blot Analysis:

Samples were prepared for electrophoresis in Laemmli sample buffer in the absence or presence of 0.1 M dithiothreitol (Laemmli, U.K. *Nature* 227:680, 1970), and separated on SDS-PAGE, using a Mini-Protean II Electrophoresis Cell (Bio-Rad, Hercules, Calif.). Protein was stained with Gel Coder® Blue Stain Reagent (Pierce, Rockford, Ill.). Electrophoretic transfer onto 0.2-μm nitrocellulose membranes was performed with a Mini Trans-Blot Cell (Bio-Rad). Membranes were incubated with either primary mouse monoclonal or rabbit polyclonal antibodies followed by HRPO-labeled secondary antibody, either goat anti-mouse IgG (Pierce) or goat anti-rabbit IgG (Pierce), as appropriate. To visualize enzyme activity, signals were developed by enhanced chemiluminescence (SuperSignal® Chemiluminescent Substrate, Pierce) and filmed.

Fibrinogen Clottability:

Clottability of the purified fibrinogen fractions was determined as previously described (Birken, S. et al., *Thromb. Res.* 7:599, 1975) using thrombin (1 U/ml) and 125 mM NaCl, 25 mM HEPES, (pH 7.4), 5 mM $CaCl_2$.

Polymerization Turbidity Curves:

Polymerization of fibrinogen species was evaluated by measuring turbidity changes with time at 340 nm using a Lambda 2 spectrophotometer (Perkin Elmer, Norwalk, Conn.) equipped with a Peltier temperature-regulated cuvette holder. Measurements were made at 25° C. in 100 μl quartz cuvettes. Data were collected with a sampling interval of 0.2 sec and analyzed using UVWINLAB software.

Factor XIIIa-catalyzed Crosslinking:

Cross-linking reactions were carried out in 125 mM NaCl, 25 mM HEPES (pH 7.4), 5 mM $CaCl_2$, at room temperature. Reactions were initiated by addition of thrombin (0.5 U/ml) to a mixture containing fibrinogen (0.36 mg/ml), either fibrinogen-420 or fibrinogen-340, and recombinant human factor XIII (10 μg/ml). Reactions were stopped at specified times by addition of Laemmli sample buffer and boiling.

Digestion with Plasmin:

Proteolysis by plasmin was conducted with substrates (0.45 mg/ml) in a buffer containing 125 mM NaCl, 25 mM HEPES, pH 7.4, 5 mM $CaCl_2$ at 37° C. Proteolysis was initiated by addition of plasmin to a final concentration of 0.03 U/ml. At specified times, aliquots were removed and the reaction stopped by mixing with Laemmli sample buffer and boiling.

RESULTS

Purification of $\alpha_E$-fibri$^{nogen}$

The paucity of positively charged amino acids in the $\alpha_E$C domains of fibrinogen-420 (Fu, Y. et al., *Biochemistry* 31:11968, 1992; Spraggon, G. et al., *Proc. Natl. Acad. Sci. USA* 95:9099, 1998) implies that the molecule will be more negatively charged than the more abundant fibrinogen-340. This difference was the rationale for attempting separation of the two species by anion exchange chromatography. As shown by the elution profile in FIG. 1, separation of human fibrinogen (fraction I-2) into two separate, unequal peaks was accomplished using a Mono Q column with a step-wise gradient of Tris Phosphate. A steep step from the starting buffer, 0.005 M Tris Phosphate, pH 8.6, to 0.2 M Tris Phosphate, pH 6.0, was immediately followed by elution of most of the protein in a single major peak (peak A). Foothills of peak A eluted during maintenance of the step for 12 column volumes. A distinct second peak (peak B) eluted approximately midway during the subsequent 12-column volume linear gradient ending at 0.5 M Tris Phosphate, pH 4.2.

Characterization of Fibrinogen Species in Peaks A and B

Figure 2A:
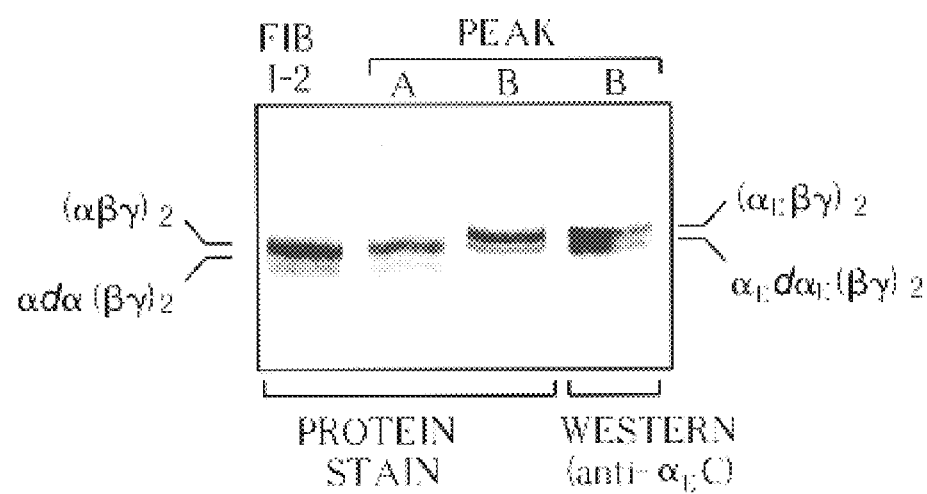
FIG. 2 is a Western analysis characterizing fibrinogen isoforms in peaks A and B. Panel A (unreduced samples) and panel B (reduced samples): Fibrinogen (Fib I-2) represents the material added and peak A and peak B the material eluted from the anion exchange column of FIG. 1. Western analysis was performed with either polyclonal anti-$\alpha_E$C #9395 or monoclonal anti-α(amino acids 603–610 of SEQ. ID Nos. 2 and 4) chain. Samples in the upper panel were electrophoresed on 4–15% SDS-PAGE gels; proteins in the lower panels were separated on homogeneous 12% SDS-PAGE gels. Positions of various hexamers (Panel A) and individual chains (Panel B) are indicated; "dα" and "dα$_E$" refer to degraded α and α$_E$, respectively. All designated α gene-derived species were recognized by 1D4, an antibody specific for an epitope in the center of the αC region (not shown).
Figure 2B:
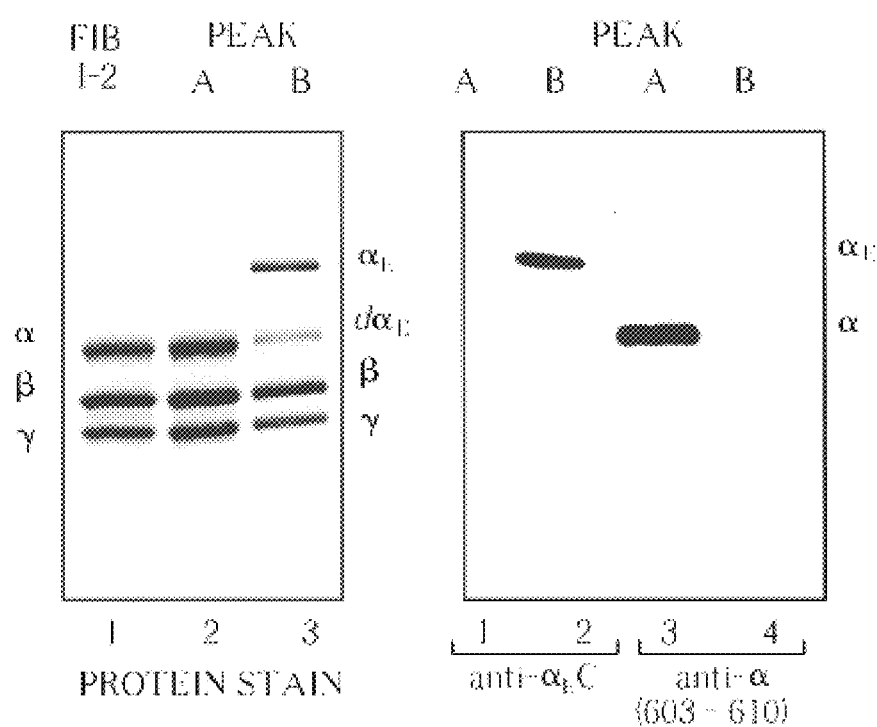

The first three fractions of peak A were pooled and compared, by SDS-PAGE and Western blot analysis, with a concentrated pool of the central three fractions of peak B (FIG. 2). The two bands visible in peak A (FIG. 2A) corresponded directly to the two most abundant species in the original fibrinogen I-2 fraction: intact and partially degraded forms of the conventional α chain-containing fibrinogen; the heterogeneity reflects the well known susceptibility of the α chains to carboxyl terminal proteolysis (Mosesson, M. W., *Ann. NY Acad. Sci.* 408:97, 1983). After its disulfide chains were reduced (FIG. 2B, left panel, lane 2), peak A resolved into the intact conventional α, β and γ bands as well as minor bands corresponding to the partially degraded α chains. Co-migration of I-2 fibrinogen and peak A bands throughout these analyses suggests that column separation did not affect the initial ratio of intact to partially degraded molecules.

In the late-eluting peak B, anti-$\alpha_E$C identified two bands (FIG. 2A, lane 4) which corresponded directly to the two bands detected by protein staining (lane 3). The proportionality between these two bands of $\alpha_E$-fibrinogen, approximately 3:1 (upper:lower), was roughly comparable to that of the two bands in peak A (lane 2), suggesting that they might also represent intact and partially proteolyzed forms.

Upon reduction of the disulfide bonds in peak B, it became clear that the $\alpha_E$-fibrinogens collectively contained not only $\alpha_E$C, β, and γ chains but also a minor band migrating at ca. 70 kDa (FIG. 2B, left panel, lane 3), just above the 68-kDa α chain of peak A (lane 2). Presumably derived from a larger species, the band was tentatively designated a degradation product (d$\alpha_E$) of the intact ca. 110-kDa $\alpha_E$ chain. It closely corresponds to the expected size of the $\alpha_E$ sequence remaining after cleavage of the $\alpha_E$C domain.

This chain assignment was confirmed by Western analysis with discriminating antibodies: anti-$\alpha_E$C #9395, which recognizes an epitope(s) unique to the extended C-terminus of $\alpha_E$ chains, and anti-α(amino acids 603–610 of SEQ. ID NO. 2 and SEQ. ID NO.: 4) chain, which is specific for the last residues of intact α chain (FIG. 2B, right panel). Anti-$\alpha_E$C recognized peak B's 110-kDa band but not its 70-kDa band (lane 2), consistent with the latter being an $\alpha_E$ chain without its carboxy terminal domain. Anti-α(amino acids 603–610 of SEQ. ID NO.: 2 and SEQ. ID NO.:4) recognized only peak A's intact α chain (lane 3), and not any of the bands in peak B (lane 4). Although intact $\alpha_E$ includes the same sequence as the terminal residues 603–610 of conventional α, it presumably escapes recognition by this antibody because the peptide bond between Val610 and Arg611 of $\alpha_E$C eliminates the free carboxyl epitope. By the same logic, the immunoreactive differences between the 68-kDa α chain and the 70-kDa band of peak B suggest that the latter is indeed an $\alpha_E$ chain cleaved at a site downstream from Val610. In this context, it should be noted that in peak B fibrinogen-420, no significant contribution of α(amino acids 1–625 of SEQ. ID NO.: 4), the conventional α chain's non-processed form (Rixon, et al., Biochemistry 22:3237, 1983 and Kant, et al., *Proc. Natl Acad Sci USA* 80:3953, 1983), was detected by Western analysis with anti-α(amino acids 615–625 of SEQ. ID NO.: 2 and SEQ. ID NO.: 4) (data not shown). Had it been present, the α(amino acids 1–625 of SEQ. ID NO.: 4) chain would have co-migrated with the 8-kDa band designated d$\alpha_E$ and, like it, escaped recognition by anti-α(amino acids 603–610 of SEQ. ID NO.: 4). It is noteworthy that, even after heavily overloading the gels, no $\alpha_E$-containing material was detectable in peak A by Western analysis with anti-$\alpha_E$C, suggesting an essentially complete separation of the two subclasses.

While a portion of the α or $\alpha_E$ chains in each peak is degraded, resulting in the minor bands labeled αdα(βγ)$_2$ and $\alpha_E$d$\alpha_E$(βγ)$_2$ in FIG. 2A, for simplicity we hereafter refer to the pooled subfractions by the nomenclature for the intact species: fibrinogen-340 for peak A, and fibrinogen-420 for peak B.

Thrombin-catalyzed Fibrin Polymerization

Figure 3:
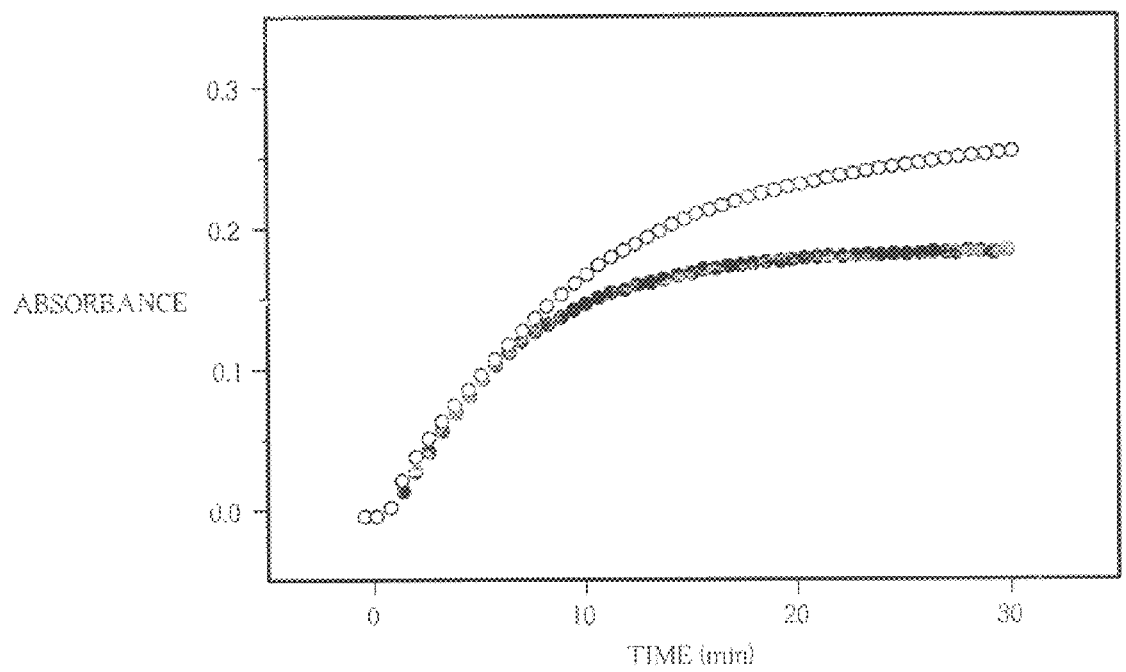
FIG. 3 is a time graph illustration of the polymerization of Fibrinogen-420 and Fibrinogen-340. Polymerization was initiated by addition of thrombin (0.1 U/ml) at time 0 to substrate at 0.1 mg/ml: either fibrinogen-420 (open circles) or fibrinogen-340 (closed circles). Polymer formation was measured as change in turbidity at 340 nm with time as described in Materials and Methods. Data are from one of three separate trials. For this set, the lag periods were 130 and 110 sec for fibrinogen-420 and fibrinogen-340, respectively, while their maximum slopes were $28 \times 10^{-5}$ sec$^{-1}$ and $37 \times 10^{-5}$ sec$^{-1}$.

When incubated with human thrombin, both fibrinogen-420 and fibrinogen-340 were found to be more than 90% clottable, forming clots that were sufficiently solid that they remained in place in inverted cuvettes. For both species, parameters of thrombin-induced clot formation were compared by monitoring turbidity as a function of time. The shapes of the turbidity curves obtained for both fibrinogen-420 and fibrinogen-340 were typical for clot formation, as seen in the representative data set of FIG. 3. Both exhibited an initial delay, followed by a rapid rise in turbidity that culminated in a plateau. Characterization by two quantitative measures—the lag period, which represents the time required for fibril formation, and the maximum slope, which reflects the rate of fibril assembly during the phase of lateral associations and branching (Hantgan, R. R. et al., *J. Biol. Chem.* 254:11272, 1979; Weisel, J. W. et al., *Biophys. J.* 63:111, 1992)—revealed little difference between the curves for fibrinogen-420 and fibrinogen-340 in three separate trials. With regard to the plateau value attained by each species, which is related to the average fiber thickness in the clot (Carr, M. E. J. et al. *Macromolecules* 11:46, 1978), outcomes were more variable and no hierarchy could be established.

Factor XIIIa-catalyzed Cross-linking

Figure 4:
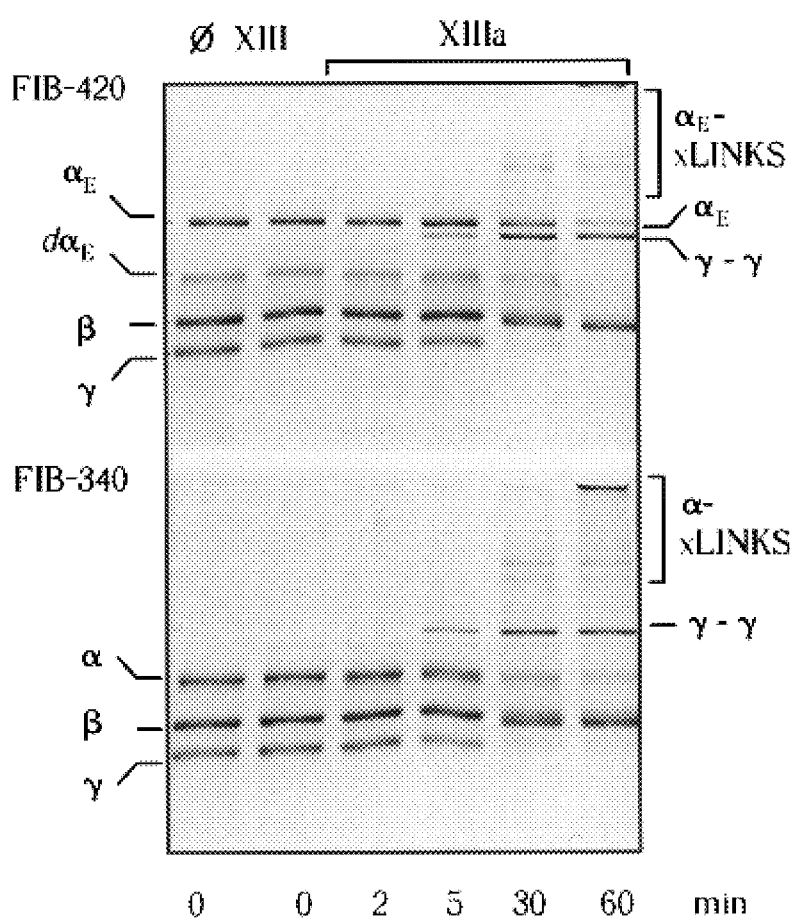
FIG. 4 is SDS-PAGE gels coupled with Western analysis of the time course of factor XIIIa-catalyzed cross-linking. Cross-linking reactions with either fibrinogen-420 (upper panel) or fibrinogen-340 (lower panel) were carried out as described in Materials and Methods. Lane 1: substrate alone. Lanes 2–6 contain substrate with either non-activated factor XIII (lane 2) or thrombin-activated factor XIIIa (lanes 3–6), incubated for 2 min (lane 3), 5 min (lane 4), 30 min (lane 5) or 60 min (lane 6). Proteins were separated on homogenous 12% SDS-PAGE gels under reducing conditions and stained. Positions of individual and cross-linked fibrinogen chains are indicated. "dα$_E$" refers to degraded α$_E$, "α$_E$-xlinks" to cross-linked α$_E$ chains, and "α-xlinks" to cross-linked α chains.

The kinetics of factor XIIIa cross-linking of fibrinogen-420 and fibrinogen-340 are compared in FIG. 4. Cross-linking of the γ chains in both preparations was essentially complete within 30 minutes, as evidenced both by the disappearance of the band corresponding to the γ chain, and the concomitant appearance of γ-dimer. Cross-linking of the α chain in fibrinogen-340 (evident from its gradual disappearance and the emergence of higher molecular weight species) occurred at a rate lagging that of the γ chain, as expected (McKee, P. A. et al., *Proc. Natl. Acad. Sci. USA* 66:738, 1970). A similarly delayed cross-linking occurred for the $\alpha_E$ and d$\alpha_E$ chains of fibrinogen-420. This observation contrasts with findings in lamprey fibrinogen where cross-linking of the $\alpha_E$ homologue (α') was considerably more efficient than for the α chain (Shipwash, E. et al., *Proc. Natl. Acad. Sci. USA* 92:968, 1995). The disparity may be due to differences in the αC regions of the lamprey fibrinogen α chain and $\alpha_E$ chain homologue which are atypically derived from separate genes (Pan, Y. et al., *Proc. Natl. Acad. Sci. USA* 89:2066, 1992; Fu, Y. et al., *Genomics* 30:71, 1995).

Example 1

Plasmic Digestion of Fibrinogen-420

Figure 5:
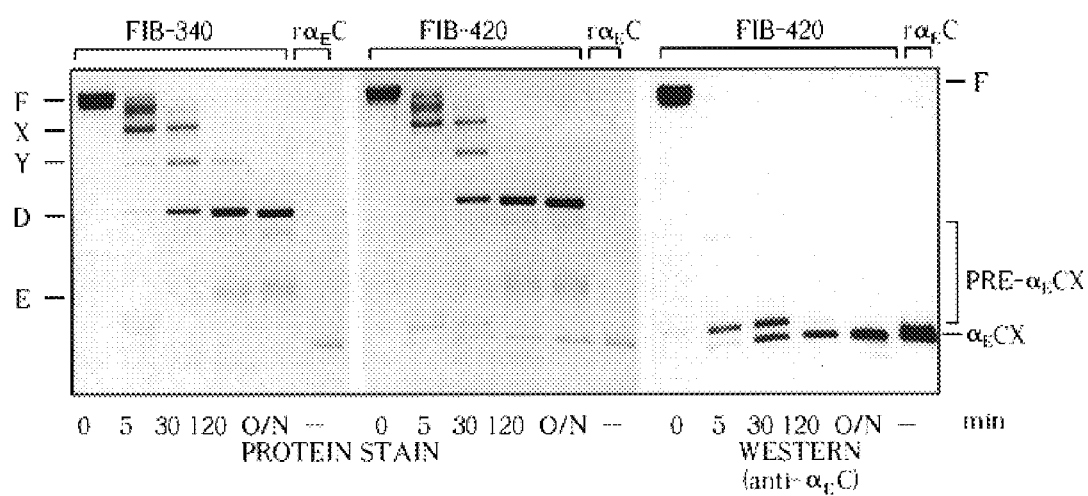
FIG. 5 is SDS-PAGE gels coupled with Western analysis of plasmin digestion of fibrinogen-420 and fibrinogen-340. The first five lanes in each panel contain purified fibrinogen (3.4 μg/lane), either fibrinogen-420 or fibrinogen-340; the sixth contains 0.5 μg of recombinant human α$_E$C (rα$_E$C) which migrates at 34 kDa (Applegate, D. et al., *Blood* 92:3669, 1998). Proteins were separated on 4–15% SDS-PAGE gels under non-reducing conditions. Left and middle panels: Gel Code® Blue Stain. Right panel: Western blot analysis of fibrinogen-420 using monoclonal anti-α$_E$C #29-1. Positions of fibrinogen (F) and fragments X, Y, D and E are indicated, as are those of the α$_E$-containing cleavage products α$_E$CX and its precursors (pre-α$_E$CX); the larger precursors can only be seen in over exposures.

Comparison of plasmic digestion of fibrinogen-420 and fibrinogen-340 by SDS-PAGE revealed very similar kinetics for production of the conventional fibrinogen degradation products: fragments X, Y, D, and E (FIG. 5, left and middle panels). However, accumulation of at least two additional products was observed in the plasmic digest of fibrinogen-420: one band ($\alpha_E$CX) co-migrating with r$\alpha_E$C, the 34-kDa yeast recombinant $\alpha_E$C domain (Applegate, D. et al., *Blood* 92:3669, 1998), and another of slower mobility, which appears to be its immediate precursor (FIG. 5, middle panel).

Both products were detected in immunoblots, using antibodies specific for the $\alpha_E C$ domain (FIG. 5, right panel). In addition, some short-lived pre-$\alpha_E CX$ species of slower mobility were observed. Cleavage of fibrinogen-420 to yield the pre-$\alpha_E CX$ species was a particularly early event in the digestion, occurring well before the appearance of significant quantities of fragments D and E. Quantitation, using r$\alpha_E C$ as a standard, suggests that the final product, $\alpha_E CX$, accumulated in molar proportion to the amount of $\alpha_E C$ present in the intact fibrinogen-420 (FIG. 5, middle panel), suggesting a degree of stability comparable to that of the core fragments D and E. Stabilization of the domain against further digestion by plasmin requires the presence of calcium (data not shown), an observation first noted for the recombinant domain (Applegate, D. et al., *Blood* 92:3669, 1998).

Example 2

Immunologic Identification of $\alpha_E CX$ Vivo

Figure 6:
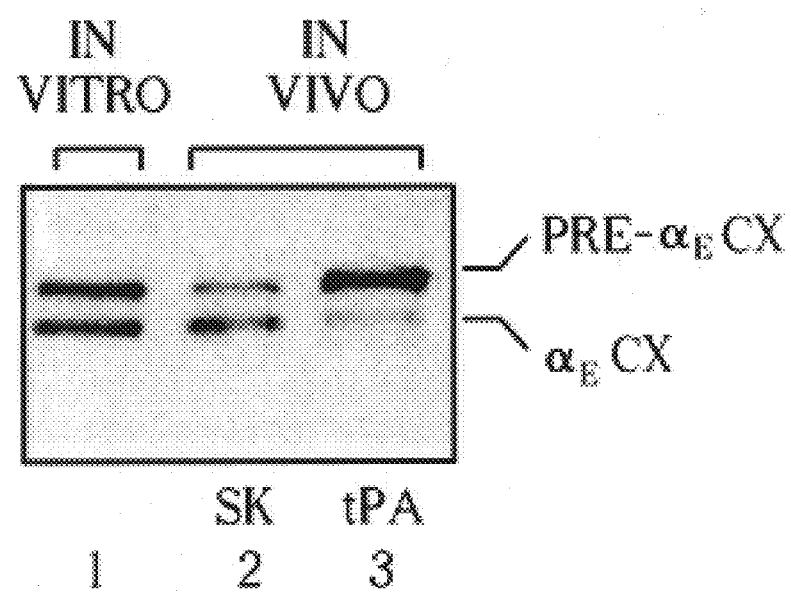
FIG. 6 is SDS-PAGE gels coupled with Western analysis showing presence of α-containing plasmin cleavage products in vivo. In vitro: a 30-min time point from plasmin digestion of purified fibrinogen-420 (see FIG. 5) In vivo: Plasma samples were collected from myocardial infarction patients 30 min into treatment with either streptokinase (SK) or tissue plasminogen activator (tPA). Proteins were separated on 10% SDS-PAGE gels under non-reducing conditions, Western blotted, and detected using monoclonal anti-α$_E$C #29-1. Positions of the split products, α$_E$CX and its precursor (pre-α$_E$CX), are indicated.

The observed in vitro stability of $\alpha_E CX$ the presence of plasmin prompted us to examine whether the fragment could also be detected in such lytic states in vivo. The generation of fibrin(ogen) degradation products is found in clinical states associated with activation of the fibrinolytic system. In particular, relatively high concentrations of fibrinolytic products have been detected in plasma of myocardial infarct patients during thrombolytic therapy with tissue plasminogen activator or streptokinase, as a result of the lytic state created during treatment. FIG. 6 shows a representative Western blot analysis, with an anti-$\alpha_E C$ antibody, of plasma obtained from myocardial infarct patients 30 minutes following treatment with either streptokinase or tissue plasminogen activator. Indeed, two bands are detected that co-migrate with $\alpha_E CX$ and its immediate precursor from plasmic digests of purified fibrinogen-420 in vitro.

This study is the first reported purification of fibrinogen-420 from human plasma, enabling a structural and functional characterization of this $\alpha_E$-containing fibrinogen subclass that constitutes a minor percentage of the circulating fibrinogen. With well separated subfractions of fibrinogen-420 and the more abundant α-fibrinogen, fibrinogen-340, we have demonstrated the overall similar behavior of these fibrinogen subclasses in clot formation and proteolytic susceptibility and have shown that plasmin attack rapidly releases the $\alpha_E C$ domain of fibrinogen-420 as an entity, $\alpha_E CX$, resistant to further degradation in vitro. Furthermore, the $\alpha_E CX$ fragment is also detectable in the plasma of patients undergoing thrombolytic therapy. On the basis of these findings, we propose that an important function(s) is discharged by the $\alpha_E C$ domain *independent of its parent fibrinogen molecule*.

The protocol described binds fraction I-2 of human fibrinogen to a Mono Q anion exchange column, eluting it in a step-wise fashion to effect a clean separation of $\alpha_E$-fibrinogen (fibrinogen-420) from α-fibrinogen (fibrinogen-340). Our SDS-PAGE analysis shows that, after purification, fibrinogen-420 is as intact as fibrinogen-340, with roughly 20% of the molecules degraded (see FIG. 2). The degradation, whether due to plasmin or other proteases (Nakashima, A. et al., *Blood Coagulation & Fibrinolysis* 3:361, 1992), occurs before the column chromatography step, either in vivo or during generation of fibrinogen fraction I-2.

By differential antibody reactivity, we have shown that conventional α chains are not incorporated into $\alpha_E$-fibrinogen from human plasma; the band in reduced $\alpha_E$-fibrinogen that migrates spuriously near the position of conventional α chains is a distinct $\alpha_E$-chain derivative which has lost a significant portion of its C-terminal domain (see FIG. 2). Thus, the native structure of $\alpha_E$-fibrinogen is indeed symmetrical, $(\alpha_E \beta \gamma)_2$, rather than mixed, $\alpha \alpha_E (\beta \gamma)_2$, and reflects a non-stochastic assembly process as noted in an earlier study (Fu, Y. et al., *Blood* 92:3302, 1998).

The closely related structures of fibrinogen-420 and fibrinogen-340 originally led us to investigate whether the $\alpha_E C$ domains of fibrinogen-420 alters the fibrinogen molecule's primary behavior in clotting and fibrinolysis. The analyses of polymerization and cross-linking presented here (FIGS. 3 and 4) show that the presence of the $\alpha_E C$ domains on a fibrinogen molecule does not grossly affect these functions. The findings support previous studies which showed that r$\alpha_E C$, the recombinant $\alpha_E C$ expressed in yeast, lacks a polymerization pocket and does not participate in cross-linking (Applegate, D. et al., *Blood* 92:3669, 1998).

Despite similarities to βC and γC, the $\alpha_E C$ domain appears to be specialized for a different function, based on several considerations. (i) While still attached to the fibrinogen core via its "αC" tether, $\alpha_E C$ undoubtedly enjoys more degrees of spatial freedom than βC or γC and consequently greater availability of its binding sites to other macromolecules. (ii) This location also appears designed to insure more rapid release of the $\alpha_E C$ domain, given the extreme susceptibility of the αC region to proteolysis (Liu, C. Y. et al., *Thromb. Haemost.* 56:100, 1986. (iii) Proteolytic release of monomeric $\alpha_E CX$ (FIG. 5) provides definitive evidence that the $\alpha_E C$ domains of fibrinogen-420 have no disulfide attachments, either to each other or to the core of the molecule, a finding consistent with the results of mutational analysis of recombinant fibrinogen-420 (Fu, Y. et al., *Blood* 92:3302, 1998) and trypsin digests of α'-fibrinogen, the counterpart to $\alpha_E$-fibrinogen in lamprey (Shipwash, E. et al., *Proc. Natl. Acad. Sci. USA* 92:968, 1995). (iv) During fibrin(ogen)olysis, the $\alpha_E C$ domains are released as monomers, unlike the βC and γC domains which remain anchored together in the proteolytic fragment D. (v) Finally, the binding clefts of the βC and γC domains contain charged/polar amino acid pairs that engage the polymerization "knobs" during fibrin assembly (Spraggon. G. et al., *Nature* 389:455, 1997; Everse, S. J. et al., *Biochemistry* 37:8637, 1998; Pratt, K. P. et al., *Proc. Natl. Acad. Sci. USA* 94:7176, 1997), whereas the corresponding cleft in the $\alpha_E C$ domain has neutral residues at its center, suggesting a different purpose (Spraggon, G. et al., *Proc. Natl. Acad. Sci. USA* 95:9099, 1998).

The $\alpha_E C$ domain is derived from exon VI, the largest conserved segment of the entire fibrinogen a gene (Fu, Y. et al., *Genomics* 30:71, 1995). In light of no discernable effect of the domain on coagulation, we suspect that preservation of $\alpha_E$ chains among higher vertebrates reflects the ability of $\alpha_E$-fibrinogen to deliver the $\alpha_E CX$ fragment to a location critical to its mission. In the recent literature, a growing number of comparable proteolytic products exhibit potent effects, unrelated to the primary function of their parent molecules which often serve to localize fragment release to sites of tissue repair, wound healing and angiogenesis (Hanahan, D. et al., *Cell* 86:353, 1996. Recent experiments with recombinant forms of $\alpha_E C$ expressed in *E. coli* (Yokoyama, K. et al., *Biochemistry* 38:5872, 1999) and yeast suggest that the domain is capable of supporting integrin-mediated cell adhesion.

The skilled artisan, therefore, will appreciate the novel $\alpha_E CX$ cleavage fragments of fibrinogen comprising an amino acid sequence set forth in: SEQ ID NO:1, SEQ ID NO:2, SEQ ID NO:3 or homologs having at least about 90% identity with SEQ ID NO:2. These examples demonstrate the above methods of detecting, and purifying $\alpha_E$CX fragments of fibrinogen. Accordingly, the $\alpha_E$CX fragments can be utilized to diagnose a fibrinolytic state or atherogenesis in a mammal, and more particularly to diagnose a myocardial infarction in a mammal. More generally, however, these $\alpha_E$CX fragments of fibrinogen can be utilized in other biological systems, and in other diseases or conditions associated with fibrinogen metabolism or pathology.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method of purifying $\alpha_E$CX fibrinogen comprising:
   providing a fibrinogen digest comprising $\alpha_E$CX fibrinogen produced by proteolytic enzyme digestion;
   contacting the digest of fibrinogen with at least one antibody that specifically binds to an $\alpha_E$C domain of fibrinogen;
   selectively removing $\alpha_E$CX fibrinogen.

2. The method according to claim 1, wherein the $\alpha_E$CX fibrinogen comprises an amino acid sequence set forth in: SEQ ID NO: 1, SEQ ID NO: 2, SEQ ID NO: 3 or homologs having at least about 90% identity with SEQ ID NO: 2.

3. The method according to claim 1, wherein said proteolytic enzyme is selected from the group consisting of fibrinolytic metalloproteinase, plasmin, u-PA, r-PA, n-PA, t-PA, streptokinase, staphylokinase, and combinations thereof.

4. A method of purifying $\alpha_E$CX fragments of fibrinogen comprising:

provliding fragments of fibrinogen comprising $\alpha_E$CX fragments of fibrinogen produced by proteolytic enzyme digestion;

contacting the fragments of fibrinogen with at least one antibody that specifically binds to an $\alpha_E$C domain of fibrinogen;

selectively removing $\alpha_E$CX fragments of fibrinogen.

5. The method according to claim 4, wherein the $\alpha_E$CX fragments of fibrinogen comprise an amino acid sequence set forth in: SEQ ID NO: 1, SEQ ID NO: 2, SEQ ID NO: 3 or homologs having at least about 90% identity with SEQ ID NO: 2.

6. An isolated $\alpha_E$CX fragment of fibrinogen having an apparent molecular weight of from about 34 to about 40 kilodaltons, or from about 36 to about 80 kilodaltons as determined by denaturing non-reducing polyacrylamide gel electrophoresis, wherein said $\alpha_E$CX fragment is bound by an antibody that specifically binds an $\alpha_E$C domain of fibrinogen, and wherein the $\alpha_E$CX fragment of fibrinogen is at least 5% pure by weight of total protein.

* * * * *

UNITED STATES PATENT AND TRADEMARK OFFICE
CERTIFICATE OF CORRECTION

PATENT NO. : 6,416,963 B1
DATED : August 22, 2002
INVENTOR(S) : Gerd Grieninger et al.

It is certified that error appears in the above-identified patent and that said Letters Patent is hereby corrected as shown below:

Title page,
Item [57], ABSTRACT,
Line 8, now reads "$\alpha_E C$", should read -- $\alpha_E CX$ --;

Column 2,
Line 8, now reads "the a subunit", should read -- the $\alpha$ subunit --;
Line 12, now reads "established a subunit", should read -- established $\alpha$ subunit --;
Line 21, now reads "236 similar to those", should read -- 236 residues providing the subunit with a globular C-terminal domain (the "VI-domain") similar to those --;

Column 7,
Line 60, now reads "Gel Code®", should read -- Gel Coder® --;

Column 9,
Line 1, now reads "lengths of the a subunit", should read -- lengths of the $\alpha$ subunit --;
Line 11, now reads "because the a subunit", should read -- because the $\alpha$ subunit --;

Column 17,
Line 19, now reads "plasma form a (aminoacids...", should read -- plasma form $\alpha$ (aminoacids... --.

Column 22,
Line 51, now reads "fibrinogen a gene", should read -- fibrinogen $\alpha$ gene --.

Signed and Sealed this

Twenty-eighth Day of January, 2003

JAMES E. ROGAN
*Director of the United States Patent and Trademark Office*

SEQUENCE LISTING

<160> NUMBER OF SEQ ID NOS: 7

<210> SEQ ID NO 1
<211> LENGTH: 251
<212> TYPE: PRT
<213> ORGANISM: Homo sapiens

<400> SEQUENCE: 1

```
Thr His Ser Thr Lys Arg Gly His Ala Lys Ser Arg Pro Val Arg Asp
 1               5                  10                  15

Cys Asp Asp Val Leu Gln Thr His Pro Ser Gly Thr Gln Ser Gly Ile
            20                  25                  30

Phe Asn Ile Lys Leu Pro Gly Ser Ser Lys Ile Phe Ser Val Tyr Cys
        35                  40                  45

Asp Gln Glu Thr Ser Leu Gly Gly Trp Leu Leu Ile Gln Gln Arg Met
    50                  55                  60

Asp Gly Ser Leu Asn Phe Asn Arg Thr Trp Gln Asp Tyr Lys Arg Gly
65                  70                  75                  80

Phe Gly Ser Leu Asn Asp Glu Gly Glu Gly Glu Phe Trp Leu Gly Asn
                85                  90                  95

Asp Tyr Leu His Leu Leu Thr Gln Arg Gly Ser Val Leu Arg Val Glu
               100                 105                 110

Leu Glu Asp Trp Ala Gly Asn Glu Ala Tyr Ala Glu Tyr His Phe Arg
           115                 120                 125

Val Gly Ser Glu Ala Glu Gly Tyr Ala Leu Gln Val Ser Ser Tyr Glu
       130                 135                 140

Gly Thr Ala Gly Asp Ala Leu Ile Glu Gly Ser Val Glu Glu Gly Ala
145                 150                 155                 160

Glu Tyr Thr Ser His Asn Asn Met Gln Phe Ser Thr Phe Asp Arg Asp
               165                 170                 175

Ala Asp Gln Trp Glu Glu Asn Cys Ala Glu Val Tyr Gly Gly Gly Trp
           180                 185                 190

Trp Tyr Asn Asn Cys Gln Ala Ala Asn Leu Asn Gly Ile Tyr Tyr Pro
       195                 200                 205

Gly Gly Ser Tyr Asp Pro Arg Asn Asn Ser Pro Tyr Glu Ile Glu Asn
   210                 215                 220

Gly Val Val Trp Val Ser Phe Arg Gly Ala Asp Tyr Ser Leu Arg Ala
225                 230                 235                 240

Val Arg Met Lys Ile Arg Pro Leu Val Thr Gln
                245                 250
```

<210> SEQ ID NO 2
<211> LENGTH: 236
<212> TYPE: PRT
<213> ORGANISM: Homo sapiens

<400> SEQUENCE: 2

-continued

```
Asp Cys Asp Asp Val Leu Gln Thr His Pro Ser Gly Thr Gln Ser Gly
 1               5                  10                  15

Ile Phe Asn Ile Lys Leu Pro Gly Ser Ser Lys Ile Phe Ser Val Tyr
            20                  25                  30

Cys Asp Gln Glu Thr Ser Leu Gly Gly Trp Leu Leu Ile Gln Gln Arg
        35                  40                  45

Met Asp Gly Ser Leu Asn Phe Asn Arg Thr Trp Gln Asp Tyr Lys Arg
    50                  55                  60

Gly Phe Gly Ser Leu Asn Asp Glu Gly Glu Gly Glu Phe Trp Leu Gly
 65                  70                  75                  80

Asn Asp Tyr Leu His Leu Leu Thr Gln Arg Gly Ser Val Leu Arg Val
                85                  90                  95

Glu Leu Glu Asp Trp Ala Gly Asn Glu Ala Tyr Ala Glu Tyr His Phe
            100                 105                 110

Arg Val Gly Ser Glu Ala Glu Gly Tyr Ala Leu Gln Val Ser Ser Tyr
        115                 120                 125

Glu Gly Thr Ala Gly Asp Ala Leu Ile Glu Gly Ser Val Glu Glu Gly
    130                 135                 140

Ala Glu Tyr Thr Ser His Asn Asn Met Gln Phe Ser Thr Phe Asp Arg
145                 150                 155                 160

Asp Ala Asp Gln Trp Glu Glu Asn Cys Ala Glu Val Tyr Gly Gly Gly
                165                 170                 175

Trp Trp Tyr Asn Asn Cys Gln Ala Ala Asn Leu Asn Gly Ile Tyr Tyr
            180                 185                 190

Pro Gly Gly Ser Tyr Asp Pro Arg Asn Asn Ser Pro Tyr Glu Ile Glu
        195                 200                 205

Asn Gly Val Val Trp Val Ser Phe Arg Gly Ala Asp Tyr Ser Leu Arg
    210                 215                 220

Ala Val Arg Met Lys Ile Arg Pro Leu Val Thr Gln
225                 230                 235
```

<210> SEQ ID NO 3
<211> LENGTH: 221
<212> TYPE: PRT
<213> ORGANISM: Homo sapiens

<400> SEQUENCE: 3

```
Gly Ile Phe Asn Ile Lys Leu Pro Gly Ser Ser Lys Ile Phe Ser Val
 1               5                  10                  15

Tyr Cys Asp Gln Glu Thr Ser Leu Gly Gly Trp Leu Leu Ile Gln Gln
            20                  25                  30

Arg Met Asp Gly Ser Leu Asn Phe Asn Arg Thr Trp Gln Asp Tyr Lys
        35                  40                  45

Arg Gly Phe Gly Ser Leu Asn Asp Glu Gly Glu Gly Glu Phe Trp Leu
    50                  55                  60

Gly Asn Asp Tyr Leu His Leu Leu Thr Gln Arg Gly Ser Val Leu Arg
 65                  70                  75                  80

Val Glu Leu Glu Asp Trp Ala Gly Asn Glu Ala Tyr Ala Glu Tyr His
                85                  90                  95

Phe Arg Val Gly Ser Glu Ala Glu Gly Tyr Ala Leu Gln Val Ser Ser
            100                 105                 110

Tyr Glu Gly Thr Ala Gly Asp Ala Leu Ile Glu Gly Ser Val Glu Glu
        115                 120                 125

Gly Ala Glu Tyr Thr Ser His Asn Asn Met Gln Phe Ser Thr Phe Asp
```

-continued

```
            130                 135                 140
Arg Asp Ala Asp Gln Trp Glu Glu Asn Cys Ala Glu Val Tyr Gly Gly
145                 150                 155                 160

Gly Trp Trp Tyr Asn Asn Cys Gln Ala Ala Asn Leu Asn Gly Ile Tyr
                165                 170                 175

Tyr Pro Gly Gly Ser Tyr Asp Pro Arg Asn Asn Ser Pro Tyr Glu Ile
            180                 185                 190

Glu Asn Gly Val Val Trp Val Ser Phe Arg Gly Ala Asp Tyr Ser Leu
            195                 200                 205

Arg Ala Val Arg Met Lys Ile Arg Pro Leu Val Thr Gln
        210                 215                 220

<210> SEQ ID NO 4
<211> LENGTH: 847
<212> TYPE: PRT
<213> ORGANISM: Homo sapiens

<400> SEQUENCE: 4

Ala Asp Ser Gly Glu Gly Asp Phe Leu Ala Glu Gly Gly Gly Val Arg
1               5                   10                  15

Gly Pro Arg Val Val Glu Arg His Gln Ser Ala Cys Lys Asp Ser Asp
                20                  25                  30

Trp Pro Phe Cys Ser Asp Glu Asp Trp Asn Tyr Lys Cys Pro Ser Gly
            35                  40                  45

Cys Arg Met Lys Gly Leu Ile Asp Glu Val Asn Gln Asp Phe Thr Asn
        50                  55                  60

Arg Ile Asn Lys Leu Lys Asn Ser Leu Phe Glu Tyr Gln Lys Asn Asn
65                  70                  75                  80

Lys Asp Ser His Ser Leu Thr Thr Asn Ile Met Glu Ile Leu Arg Gly
                85                  90                  95

Asp Phe Ser Ser Ala Asn Asn Arg Asp Asn Thr Tyr Asn Arg Val Ser
            100                 105                 110

Glu Asp Leu Arg Ser Arg Ile Glu Val Leu Lys Arg Lys Val Ile Glu
        115                 120                 125

Lys Val Gln His Ile Gln Leu Leu Gln Lys Asn Val Arg Ala Gln Leu
130                 135                 140

Val Asp Met Lys Arg Leu Glu Val Asp Ile Asp Ile Lys Ile Arg Ser
145                 150                 155                 160

Cys Arg Gly Ser Cys Ser Arg Ala Leu Ala Arg Glu Val Asp Leu Lys
                165                 170                 175

Asp Tyr Glu Asp Gln Gln Lys Gln Leu Glu Gln Val Ile Ala Lys Asp
            180                 185                 190

Leu Leu Pro Ser Arg Asp Arg Gln His Leu Pro Leu Ile Lys Met Lys
        195                 200                 205

Pro Val Pro Asp Leu Val Pro Gly Asn Phe Lys Ser Gln Leu Gln Lys
    210                 215                 220

Val Pro Pro Glu Trp Lys Ala Leu Thr Asp Met Pro Gln Met Arg Met
225                 230                 235                 240

Glu Leu Glu Arg Pro Gly Gly Asn Glu Ile Thr Arg Gly Gly Ser Thr
                245                 250                 255

Ser Tyr Gly Thr Gly Ser Glu Thr Glu Ser Pro Arg Asn Pro Ser Ser
            260                 265                 270

Ala Gly Ser Trp Asn Ser Gly Ser Ser Gly Pro Gly Ser Thr Gly Asn
        275                 280                 285
```

-continued

```
Arg Asn Pro Gly Ser Ser Gly Thr Gly Thr Ala Thr Trp Lys Pro
    290                 295                 300
Gly Ser Ser Gly Pro Gly Ser Thr Gly Ser Trp Asn Ser Gly Ser Ser
305                 310                 315                 320
Gly Thr Gly Ser Thr Gly Asn Gln Asn Pro Gly Ser Pro Arg Pro Gly
                325                 330                 335
Ser Thr Gly Thr Trp Asn Pro Gly Ser Ser Glu Arg Gly Ser Ala Gly
            340                 345                 350
His Trp Thr Ser Glu Ser Ser Val Ser Gly Ser Thr Gly Gln Trp His
        355                 360                 365
Ser Glu Ser Gly Ser Phe Arg Pro Asp Ser Pro Gly Ser Gly Asn Ala
    370                 375                 380
Arg Pro Asn Asn Pro Asp Trp Gly Thr Phe Glu Val Ser Gly Asn
385                 390                 395                 400
Val Ser Pro Gly Thr Arg Arg Glu Tyr His Thr Glu Lys Leu Val Thr
                405                 410                 415
Ser Lys Gly Asp Lys Glu Leu Arg Thr Gly Lys Glu Lys Val Thr Ser
            420                 425                 430
Gly Ser Thr Thr Thr Arg Arg Ser Cys Ser Lys Thr Val Thr Lys
        435                 440                 445
Thr Val Ile Gly Pro Asp Gly His Lys Glu Val Thr Lys Glu Val Val
    450                 455                 460
Thr Ser Glu Asp Gly Ser Asp Cys Pro Glu Ala Met Asp Leu Gly Thr
465                 470                 475                 480
Leu Ser Gly Ile Gly Thr Leu Asp Gly Phe Arg His Arg His Pro Asp
                485                 490                 495
Glu Ala Ala Phe Phe Asp Thr Ala Ser Thr Gly Lys Thr Phe Pro Gly
            500                 505                 510
Phe Phe Ser Pro Met Leu Gly Glu Phe Val Ser Glu Thr Glu Ser Arg
        515                 520                 525
Gly Ser Glu Ser Gly Ile Phe Thr Asn Thr Lys Glu Ser Ser Ser His
    530                 535                 540
His Pro Gly Ile Ala Glu Phe Pro Ser Arg Gly Lys Ser Ser Ser Tyr
545                 550                 555                 560
Ser Lys Gln Phe Thr Ser Ser Thr Ser Tyr Asn Arg Gly Asp Ser Thr
                565                 570                 575
Phe Glu Ser Lys Ser Tyr Lys Met Ala Asp Glu Ala Gly Ser Glu Ala
            580                 585                 590
Asp His Glu Gly Thr His Ser Thr Lys Arg Gly His Ala Lys Ser Arg
        595                 600                 605
Pro Val Arg Asp Cys Asp Asp Val Leu Gln Thr His Pro Ser Gly Thr
    610                 615                 620
Gln Ser Gly Ile Phe Asn Ile Lys Leu Pro Gly Ser Ser Lys Ile Phe
625                 630                 635                 640
Ser Val Tyr Cys Asp Gln Glu Thr Ser Leu Gly Gly Trp Leu Leu Ile
                645                 650                 655
Gln Gln Arg Met Asp Gly Ser Leu Asn Phe Asn Arg Thr Trp Gln Asp
            660                 665                 670
Tyr Lys Arg Gly Phe Gly Ser Leu Asn Asp Glu Gly Glu Gly Glu Phe
        675                 680                 685
Trp Leu Gly Asn Asp Tyr Leu His Leu Leu Thr Gln Arg Gly Ser Val
    690                 695                 700
Leu Arg Val Glu Leu Glu Asp Trp Ala Gly Asn Glu Ala Tyr Ala Glu
```

```
                705                  710                 715                 720
Tyr His Phe Arg Val Gly Ser Glu Ala Glu Gly Tyr Ala Leu Gln Val
                        725                 730                 735
Ser Ser Tyr Glu Gly Thr Ala Gly Asp Ala Leu Ile Glu Gly Ser Val
            740                 745                 750
Glu Glu Gly Ala Glu Tyr Thr Ser His Asn Asn Met Gln Phe Ser Thr
        755                 760                 765
Phe Asp Arg Asp Ala Asp Gln Trp Glu Glu Asn Cys Ala Glu Val Tyr
    770                 775                 780
Gly Gly Gly Trp Trp Tyr Asn Asn Cys Gln Ala Ala Asn Leu Asn Gly
785                 790                 795                 800
Ile Tyr Tyr Pro Gly Gly Ser Tyr Asp Pro Arg Asn Asn Ser Pro Tyr
                805                 810                 815
Glu Ile Glu Asn Gly Val Val Trp Val Ser Phe Arg Gly Ala Asp Tyr
            820                 825                 830
Ser Leu Arg Ala Val Arg Met Lys Ile Arg Pro Leu Val Thr Gln
        835                 840                 845
```

<210> SEQ ID NO 5
<211> LENGTH: 2648
<212> TYPE: DNA
<213> ORGANISM: Homo sapiens

<400> SEQUENCE: 5

```
atgttttcca tgaggatcgt ctgcctagtt ctaagtgtgg tgggcacagc atggactgca      60
gatagtggtg aaggtgactt tctagctgaa ggaggaggcg tactgcagat agtggtgaag     120
gtgactttct agctgaagga ggaggcgtgc gtggcccaag ggttgtggaa agacatcaat     180
ctgcctgcaa agattcagac tggcccttct gctctgatga agactggaac tacaaatgcc     240
cttctggctg caggatgaaa gggttgattg atgaagtcaa tcaagatttt acaaacagaa     300
taaataagct caaaaattca ctatttgaat atcagaagaa caataaggat tctcattcgt     360
tgaccactaa tataatggaa attttgagag gcgattttc ctcagccaat aaccgtgata     420
atacctacaa ccgagtgtca gaggatctga aagcagaat tgaagtcctg aagcgcaaag     480
tcatagaaaa agtacagcat atccagcttc tgcagaaaaa tgttagagct cagttggttg     540
atatgaaacg actggaggtg acattgata ttaagatccg atcttgtcga gggtcatgca     600
gtagggcttt agctcgtgaa gtagatctga aggactatga agatcagcag aagcaacttg     660
aacaggtcat tgccaaagac ttacttccct ctagagatag gcaacactta ccactgataa     720
aaatgaaacc agttccagac ttggttcccg gaaattttaa gagccagctt cagaaggtac     780
ccccagagtg gaaggcatta acagacatgc cgcagatgag aatggagtta gagagacctg     840
gtggaaatga gattactcga ggaggctcca cctcttatgg aaccggatca gagacggaaa     900
gccccaggaa ccctagcagt gctggaagct ggaactctgg gagctctgga cctggaagta     960
ctggaaaccg aaaccctggg agctctggga ctggagggac tgcaacctgg aaacctggga    1020
gctctggacc tggaagtact ggaagctgga actctggag ctctggaact ggaagtactg    1080
gaaaccaaaa ccctgggagc cctagacctg gtagtaccgg aacctggaat cctggcagct    1140
ctgaacgcgg aagtgctggg cactggacct ctgagagctc tgtatctggt agtactggac    1200
aatggcactc tgaatctgga gttttaggc cagatagccc aggctctggg aacgcgaggc    1260
ctaacaaccc agactgggc acatttgaag aggtgtcagg aaatgtaagt ccaggacaa     1320
ggagagagta ccacacagaa aaactggtca cttctaaagg agataaagag ctcaggactg    1380
```

```
gtaaagagaa ggtcacctct ggtagcacaa ccaccacgcg tcgttcatgc tctaaaaccg      1440
ttactaagac tgttattggt cctgatggtc acaaagaagt taccaaagaa gtggtgacct      1500
ccgaagatgg ttctgactgt cccgaggcaa tggatttagg cacattgtct ggcataggta      1560
ctctggatgg gttccgccat aggcaccctg atgaagctgc cttcttcgac actgcctcaa      1620
ctggaaaaac attcccaggt ttcttctcac ctatgttagg agagtttgtc agtgagactg      1680
agtctagggg ctcagaatct ggcatcttca caaatacaaa ggaatccagt tctcatcacc      1740
ctgggatagc tgaattccct tcccgtggta aatcttcaag ttacagcaaa caatttacta      1800
gtagcacgag ttacaacaga ggagactcca catttgaaag caagagctat aaaatggcag      1860
atgaggccgg aagtgaagcc gatcatgaag gaacacatag caccaagaga ggccatgcta      1920
aatctcgccc tgtcagagac tgtgatgatg tcctccaaac acatccttca ggtacccaaa      1980
gtggcatttt caatatcaag ctaccgggat ccagtaagat tttttctgtt tattgcgatc      2040
aagagaccag tttgggagga tggcttttga tccagcaaag aatggatgga tcactgaatt      2100
ttaaccggac ctggcaagac tacaagagag gtttcggcag cctgaatgac gagggggaag      2160
gagaattctg gctaggcaat gactacctcc acttactaac ccaaaggggc tctgttctta      2220
gggttgaatt agaggactgg gctgggaatg aagcttatgc agaatatcac ttccgggtag      2280
gctctgaggc tgaaggctat gccctccaag tctcctccta tgaaggcact gcgggtgatg      2340
ctctgattga gggttccgta gaggaagggg cagagtacac ctctcacaac aacatgcagt      2400
tcagcacctt tgacagggat gcagaccagt gggaagagaa ctgtgcagaa gtctatgggg      2460
gaggctggtg gtataataac tgccaagcag ccaatctcaa tggaatctac taccctgggg      2520
gctcctatga cccaaggaat aacagtcctt atgagattga gaatggagtg gtctgggttt      2580
cctttagagg ggcagattat tccctcaggg ctgttcgcat gaaaattagg ccccttgtga      2640
cccaatag                                                              2648
```

<210> SEQ ID NO 6
<211> LENGTH: 11
<212> TYPE: PRT
<213> ORGANISM: Homo sapiens

<400> SEQUENCE: 6

Thr Ser Pro Leu Gly Lys Pro Ser Leu Ser Pro
  1               5                  10

<210> SEQ ID NO 7
<211> LENGTH: 8
<212> TYPE: PRT
<213> ORGANISM: Homo sapiens

<400> SEQUENCE: 7

Gly His Ala Lys Ser Arg Pro Val
  1               5